(12) United States Patent
Hames et al.

(10) Patent No.: US 11,640,854 B1
(45) Date of Patent: May 2, 2023

(54) GENERATION AND DELIVERY OF CUSTOMIZED CONTENT PROGRAMS

(71) Applicant: Big Health Inc., San Francisco, CA (US)

(72) Inventors: Peter A. Hames, San Francisco, CA (US); Colin Espie, Glasgow (GB); Kelvin Kwong, San Francisco, CA (US); Jenna Rae Carl, San Francisco, CA (US); Killian O'Connell, London (GB)

(73) Assignee: Big Health Inc., San Francisco, CA (US)

( * ) Notice: Subject to any disclaimer, the term of this patent is extended or adjusted under 35 U.S.C. 154(b) by 3 days.

(21) Appl. No.: 17/157,261

(22) Filed: Jan. 25, 2021

Related U.S. Application Data

(63) Continuation of application No. 16/554,382, filed on Aug. 28, 2019, now Pat. No. 10,902,942.
(Continued)

(51) Int. Cl.
*G16H 20/00* (2018.01)
*G16H 20/70* (2018.01)
(Continued)

(52) U.S. Cl.
CPC ....... *G16H 20/00* (2018.01); *G06F 16/24565* (2019.01); *G06F 16/335* (2019.01); *G06F 16/3337* (2019.01); *G06F 16/9024* (2019.01); *G09B 7/00* (2013.01); *G09B 7/06* (2013.01); *G09B 7/08* (2013.01); *G16H 10/20* (2018.01); *G16H 20/70* (2018.01); *G16H 50/00* (2018.01);
(Continued)

(58) Field of Classification Search
CPC ......... G06F 16/24565; G06F 16/24578; G06F 16/248; G06F 16/3337; G06F 16/335; G06F 16/9024; G09B 7/00; G09B 7/06; G09B 7/08; G16H 20/00; G16H 20/70; G16H 50/00; G16H 50/20; G16H 50/30; G16H 10/20; G01N 2800/30
See application file for complete search history.

(56) References Cited

U.S. PATENT DOCUMENTS 6,165,126 A * 12/2000 Merzenich ............. G16H 70/60
600/300
6,425,764 B1 7/2002 Lamson
(Continued)

FOREIGN PATENT DOCUMENTS

WO 2005/029350 A1 3/2005

OTHER PUBLICATIONS

First Action Interview Pilot Program Pre-Interview Communication dated Dec. 2, 2019 in related U.S. Appl. No. 16/554,382, all pgs.
(Continued)

*Primary Examiner* — Diedra McQuitery
(74) *Attorney, Agent, or Firm* — Kilpatrick Townsend & Stockton

(57) ABSTRACT

Provided are systems, methods, and computer-readable medium for obtaining specific information about one or more psychological conditions. The information is obtained in a manner such that a second response is based on a first response. Once the information has been obtained, a customized content program for responding to the one or more psychological conditions may be generated.

20 Claims, 12 Drawing Sheets

Related U.S. Application Data

(60) Provisional application No. 62/738,955, filed on Sep. 28, 2018, provisional application No. 62/738,952, filed on Sep. 28, 2018, provisional application No. 62/724,283, filed on Aug. 29, 2018.

(51) Int. Cl.

| | | |
|---|---|---|
| *G16H 10/20* | (2018.01) | |
| *G16H 50/30* | (2018.01) | |
| *G16H 50/00* | (2018.01) | |
| *G09B 7/06* | (2006.01) | |
| *G09B 7/08* | (2006.01) | |
| *G09B 7/00* | (2006.01) | |
| *G06F 16/901* | (2019.01) | |
| *G06F 16/335* | (2019.01) | |
| *G06F 16/2455* | (2019.01) | |
| *G06F 16/33* | (2019.01) | |
| *G06F 16/2457* | (2019.01) | |
| *G06F 16/248* | (2019.01) | |
| *G16H 50/20* | (2018.01) | |

(52) U.S. Cl.
CPC ......... *G16H 50/30* (2018.01); *G01N 2800/30* (2013.01); *G06F 16/248* (2019.01); *G06F 16/24578* (2019.01); *G16H 50/20* (2018.01)

(56) References Cited

U.S. PATENT DOCUMENTS

| | | | |
|---|---|---|---|
| 7,314,451 | B2 | 1/2008 | Halperin et al. |
| 8,403,865 | B2 | 3/2013 | Halperin et al. |
| 8,589,328 | B1 | 11/2013 | Sharma |
| 8,992,434 | B2 | 3/2015 | Halperin et al. |
| 9,223,837 | B2 | 12/2015 | Djugash |
| 9,474,481 | B2 | 10/2016 | Dagum |
| 9,633,175 | B2 | 4/2017 | Hames et al. |
| 10,902,942 | B1 | 1/2021 | Hames |
| 2002/0035486 | A1 | 3/2002 | Huyn |
| 2003/0059750 | A1 | 3/2003 | Bindler |
| 2005/0245790 | A1 | 11/2005 | Bergfalk et al. |
| 2006/0241510 | A1 | 10/2006 | Halperin et al. |
| 2008/0208015 | A1 | 8/2008 | Morris et al. |
| 2008/0269625 | A1 | 10/2008 | Halperin et al. |
| 2011/0190594 | A1 | 8/2011 | Heit |
| 2012/0287035 | A1 | 11/2012 | Valko et al. |
| 2013/0123571 | A1 | 5/2013 | Doman |
| 2014/0065585 | A1 | 3/2014 | Osborn |
| 2014/0222720 | A1 | 8/2014 | Hames |
| 2015/0149200 | A1 | 5/2015 | Kerssens |
| 2015/0154372 | A1* | 6/2015 | Soenksen ............... G16H 50/30 705/2 |
| 2016/0022193 | A1* | 1/2016 | Rau ....................... A61B 5/4884 600/595 |
| 2016/0040470 | A1 | 2/2016 | Castro et al. |
| 2016/0143571 | A1 | 5/2016 | Suddamalla et al. |
| 2016/0210440 | A1 | 7/2016 | Munafo et al. |
| 2016/0210839 | A1 | 7/2016 | Yadav |
| 2017/0004260 | A1 | 1/2017 | Moturu |
| 2017/0017759 | A1 | 1/2017 | MacNeice et al. |
| 2017/0202486 | A1 | 7/2017 | Martikka et al. |
| 2017/0220774 | A1* | 8/2017 | Orbach ................. G16H 10/20 |
| 2017/0235912 | A1* | 8/2017 | Moturu ................. G16H 40/67 705/2 |
| 2017/0332948 | A1 | 11/2017 | Weffers-Albu et al. |
| 2017/0365101 | A1 | 12/2017 | Samec |
| 2018/0366142 | A1* | 12/2018 | Ashoori ................. A61B 5/11 |
| 2019/0043610 | A1 | 2/2019 | Vaughan |
| 2019/0074081 | A1* | 3/2019 | Easton .................. G06Q 10/10 |
| 2019/0189259 | A1* | 6/2019 | Clark .................... G16H 10/60 |
| 2019/0243944 | A1* | 8/2019 | Jain ....................... G16H 80/00 |
| 2019/0374157 | A1* | 12/2019 | McGinnis ........... A61B 5/02438 |
| 2020/0184158 | A1* | 6/2020 | Kuczmarski ........... G06N 3/084 |

OTHER PUBLICATIONS

Notice of Allowance dated Feb. 13, 2020 in related U.S. Appl. No. 16/554,382, all pgs.
Non-Final Office Action dated Jun. 29, 2020 in related U.S. Appl. No. 16/554,382, all pgs.
Notice of Allowance dated Oct. 1, 2020 in related U.S. Appl. No. 16/554,382, all pgs.
Website: "https://www.zansors.com/help4-more/", Zansor Personal Health Analytics, Zansors, LLC, Arlington, VA, retrieved Sep. 23, 2019.
Website: "https://www.superbetter.com/", SuperBetter, LLC., Wheaton, IL, retrieved Sep. 24, 2019.
Website: https://jitters.co/, TwoThirtySix Labs, LLC., Austin, TX, retrieved Sep. 24, 2019.
Website: "http://www.virtuallybetter.com/"., Virtually Better, Inc. Decatur, GA, retrieved Sep. 24, 2019.
Website: "https://www.yesdelft.com/startups/clevr/,", Yes!Delft,, Molengraaffsingel 12, 2629 JD Delft, retrieved Sep. 24, 2019.
Website: https://mimerse.com/, Mimerse AB, Stockholm Sweden, retrieved Sep. 24, 2019.
Website: https://vrphobia.com/, Virtual Reality Medical Center, (VRMC), San Diego, CA, retrieved Sep. 24, 2019.
Website of "The Virtual Reality Medical Center", https://vrphobia.com/, frontoffice@vrphobia.com, copyright © 2022 Virtual Reality Medical Center (VRMC), 6540 lusk Boulevard, Suite C115, San Deiego, CA, 92121. Retrieved from the internet on Apr. 8, 2022, 1 page.

* cited by examiner

GENERATION AND DELIVERY OF CUSTOMIZED CONTENT PROGRAMS

CROSS-REFERENCE TO RELATED APPLICATIONS

This application is a continuation of U.S. patent application Ser. No. 16/554,382, filed Aug. 28, 2019, entitled "Generation And Delivery Of Customized Content Programs," which application claims priority to U.S. Provisional Patent Application No. 62/724,283, filed on Aug. 29, 2018, entitled "Transdiagnostic Digital Medicine System," U.S. Provisional Patent Application No. 62/738,952, filed on Sep. 28, 2018, entitled "Customized Content Delivery System," and U.S. Provisional Patent Application No. 62/738,955, filed on Sep. 28, 2018, entitled "Customized Content Presentation System," the disclosures of which are hereby incorporated by reference in their entirety for all purposes.

BACKGROUND

Computing devices and computing systems may be used to deliver content of various types. For example, a content delivery service may provide content over a network to user devices, such as smart phones, tablet computers, and other handheld computing devices, as well as desktop computers, laptop computers, internet televisions, game consoles, and other network-connected computing devices. The content may be multimedia content, and thus may include audio, moving video, and/or still images. The content may, alternatively or additionally, be interactive, such that the content reacts to a user's inputs.

In some examples, the content delivery service may be hosted at a data center, with the content delivered by the service being stored on storage devices of the data center. Alternatively or additionally, in some examples, the content delivery service may be hosted on compute servers of an enterprise network. In these and other examples, the content delivery service may transmit content to an application executing on a user computer device when the content is requested by the application.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method for content delivery, including transmitting, by a content delivery service executing on a computing system, a series of queries to a computing device on a network, where a first set of queries of the series of queries is of a first query type, and where the computing device displays the series of queries in an application executing on the computing device. The computer-implemented method also includes receiving, by the content delivery service and from the computing device, responses to the series of queries. The computer-implemented method also includes determining, by the content delivery service and using the responses, scores for each of a set of drivers, where each driver includes a factor associated with one or more psychological issues, where the set of drivers is associated with a plurality of content sessions, and where at least one content session of the plurality of content sessions includes a multimedia presentation relating to cognitive behavioral therapy. The computer-implemented method also includes selecting, by the content delivery service and using the scores, particular content sessions from the plurality of content sessions. The computer-implemented method also includes determining, by the content delivery service, an order and a schedule for presenting the particular content sessions based on the scores and drivers associated with the particular content sessions. The computer-implemented method also includes determining, by the content delivery service, a customized content program based on the particular content sessions, the order, and the schedule for presenting the particular content sessions. The computer-implemented method also includes outputting, by the content delivery service, the customized content program to the computing device according to the order and the schedule. Other examples of this aspect include corresponding computer systems, apparatus, and computer programs recorded on one or more computer storage devices, each configured to perform the actions of the methods.

One general aspect includes a computer-implemented method for content delivery, including reading, by a content delivery service executing on a computing system, a series of queries from a storage device associated with the content delivery service. The computer-implemented method also includes transmitting, by the content delivery service, the series of queries to a computing device, where the computing device displays the series of queries in an application executing on the computing device, and where each query is displayed with a prompt for a response. The computer-implemented method also includes receiving, by the content delivery service and from the computing device, a first set of responses to a first set of queries from the series of queries. The computer-implemented method also includes determining, by the content delivery service and using the first set of responses, a program of content, the program of content including a series of content sessions, where each content session is related to cognitive behavioral therapy and includes at least one of an audio segment, a video segment, an interactive multimedia module, or a question. The computer-implemented method also includes determining, using the first set of responses, a first content session of the program of content that will be presented at the computing device. The computer-implemented method also includes receiving, by the content delivery service and from the computing device, a second set of responses to a second set of queries from the series of queries. The computer-implemented method also includes determining, by the content delivery service and using at least one of the first set of responses or the second set of responses, a customization for the first content session of the program of content. The computer-implemented method also includes determining, by the content delivery service, a presentation for the program of content. The computer-implemented method also includes transmitting, by the content delivery service and to the computing device, the presentation for the program of content and the customization for the first content session, where the computing device renders the presentation in a context layer of the application, and where the context layer modifies an appearance of the first content session. Other examples of this aspect include corresponding computer systems, apparatus, and computer programs recorded on one or more computer storage devices, each configured to perform the actions of the methods.

BRIEF DESCRIPTION OF THE DRAWINGS

Examples are described in detail below with reference to the following figures.

DETAILED DESCRIPTION

The ensuing description provides preferred exemplary example(s) only, and is not intended to limit the scope, applicability or configuration of the disclosure. Rather, the ensuing description of the preferred exemplary example(s) will provide those skilled in the art with an enabling description for implementing a preferred exemplary example. It is understood that various changes may be made in the function and arrangement of elements without departing from the spirit and scope as set forth in the appended claims.

Figure 1:
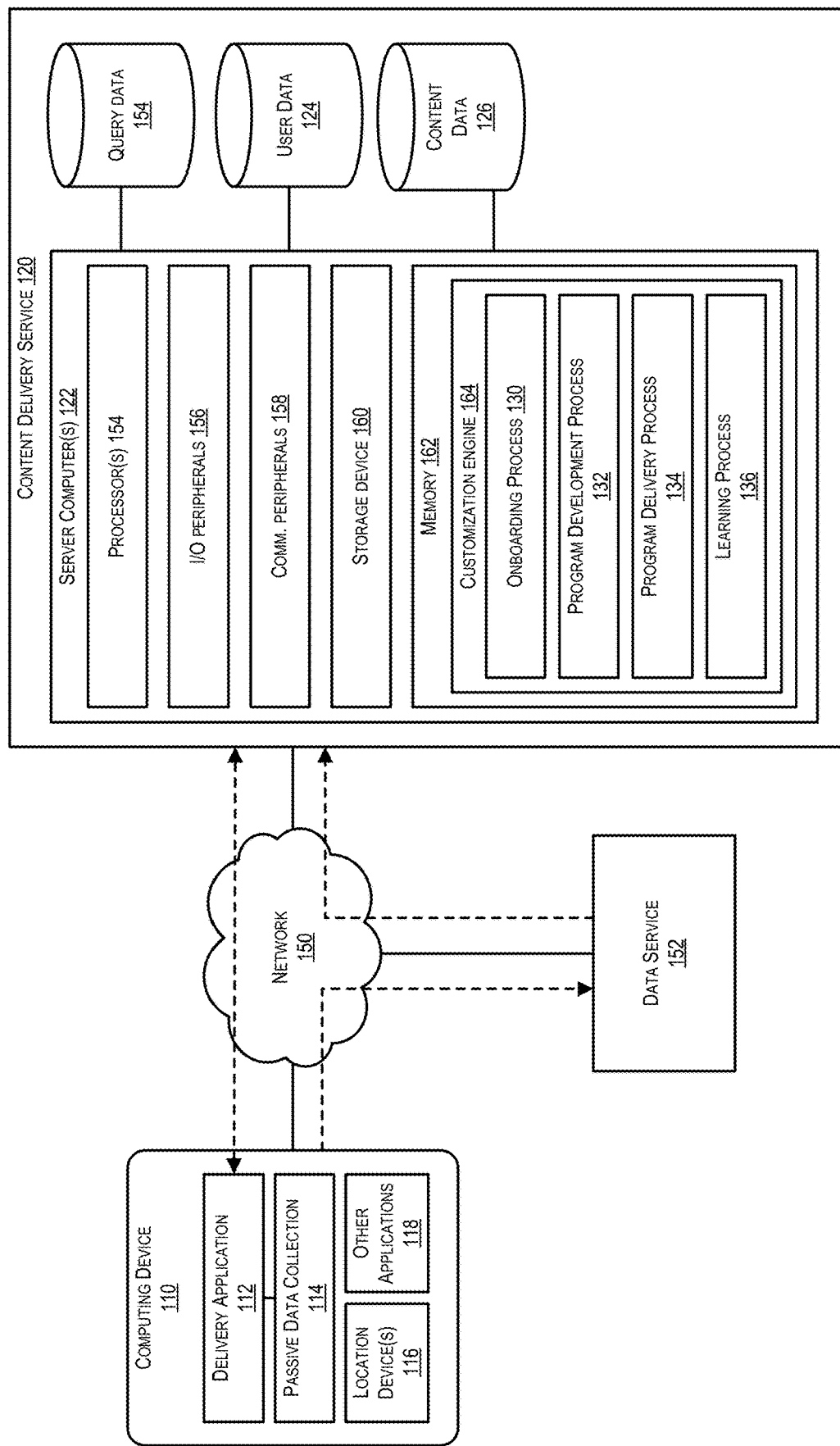
FIG. 1 includes an example block diagram illustrating an example of a content delivery system that may be used to implement techniques relating to generating and transmitting customized programs of content to computing devices, according to at least one example.

FIG. 1 includes an example block diagram illustrating an example of a content delivery system 100 that may be used to implement techniques relating to generating and transmitting customized programs of content to computing devices, according to at least one example. In some examples, the content delivery system 100 may be used to deliver a digital cognitive behavioral therapy (CBT) in customized content presentations. In various examples, the content delivery system 100 includes a content delivery service 120 that may provide content to computing devices, such as a computing device 110 illustrated in the example. In various examples, the content delivery service 120 may communicate with the computing device 110 over a network 150, which may include private networks and/or public networks such as the Internet. In some examples, the content delivery service 120 may optionally communicate over the network 150 with a data service 152 that may provide data about the computing device 110.

The computing device 110 of this example may include various types of electronic devices that include a microprocessor capable of executing instructions of computing code, memory for storing the instructions and/or other data, and network capability, such as a wired or wireless network card and/or a cellular antenna. Examples of such electronic devices include laptop computers, desktop computers, tablet computers, smart phones, personal digital assistants, smart watches, digital eyeglass systems, internet televisions, game consoles, and others.

The computing device 110 may be associated with one user or multiple users. A user, in this context, is a digital entity that is maintained by a computing system, and for which various types of digital identifiers may exist that associate data with the user. For example, a user may be identified to a computing system by a username, which may be an alphanumeric string. In this example, the username may be associated with a user account on the computing system and/or on a network. The user account may further be associated with authentication data, such as a password, a security token, bioinformatic data, or other data that may be used to give a person access to the account, or to give the account access to the computing system. As another example, a user may be identified by an email address, a social media handle (e.g., a type of username), a gaming handle, a mobile telephone number, or another type of identifier. In some examples, one user may be associated with multiple user accounts. In some examples, one user may be associated with multiple email addresses, social media handles, or other identifiers. In some examples, more than one person (e.g., a human being) may be associated with the same user. For example, a team of network administrators may each have access to the same user account.

In various examples, the computing device 110 includes hardware and software that enable the computing device 110 to interact with the content delivery service 120 and receive content. For example, the computing device 110 may include a delivery application 112 through which a user may interact with the content delivery service 120 to obtain content. The delivery application 112 may be provided by the content delivery service 120. The delivery application 112 may include a graphical user interface that may be output using a display of the device 110, and through which a user may enter input. To obtain feedback about the user's interaction with the content delivery service 120, the delivery application 112 may include a passive data collection 114 component. The passive data collection 114 may record information such as times and day when the delivery application 112 is launched, the content retrieved from the content delivery service 120 and output in the delivery application 112, the amount of time the user spends in the delivery application 112, and other information. Additional information may also be collected about the computing device 110, which may be used to change the content delivered through the delivery application 112. For example, the computing device 110 may also include one or more location devices 116 that may determine the computing device's location, and that produce location data. The location data may be used by the content delivery service 120 for various purposes, such as changing a user's content program, or interactively suggesting content, among other examples. Other examples of additional information include data from accelerometers, gyroscopes, heart rate monitors, scheduling, and any other application or sensor of the computing device 110. In some examples, the additional information may be obtained from sensors of applications of an accessory device. For example, the computing device 110 may be associated with a smartwatch, which may include various sensors and may provide sensor data to the computing device 110.

In various examples, the content delivery service 120 may be implemented using various software processes executing on or more server computers 122. The one or more server computers 122 may be a single computer and/or can represent a distributed computing system such as one or more server computing devices. The server computer 122 includes a processor 154, a memory 162, a storage device 160, input/output peripherals (I/O) 156, and communication peripherals 158.

The memory 162 and the storage device 160 include computer-readable storage media, such as Radom Access Memory (RAM), Read ROM, electrically erasable programmable read-only memory (EEPROM), hard drives, CD-ROMs, optical storage devices, magnetic storage devices, electronic non-volatile computer storage, for example Flash® memory, and other tangible storage media. Any of such computer-readable storage media can be configured to store instructions or program codes embodying aspects of the disclosure. The memory 162 and the storage device 160 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with the server computer 122.

Further, the memory 162 includes an operating system, programs, and applications. The processor 154 is configured to execute the stored instructions and includes, for example, a logical processing unit, a microprocessor, a digital signal processor, and other processors. The memory 162 and/or the processor 154 can be virtualized and can be hosted within another computing system of, for example, a cloud network or a data center. The I/O peripherals 156 include user interfaces, such as a keyboard, screen (e.g., a touch screen), microphone, speaker, other input/output devices, and computing components, such as graphical processing units, serial ports, parallel ports, universal serial buses, and other input/output peripherals. The I/O peripherals 156 are connected to the processor 154. The communication peripherals 158 are configured to facilitate communication between the server computer 122 and other computing devices over a communications network and include, for example, a network interface controller, modem, wireless and wired interface cards, antenna, and other communication peripherals.

The memory 162 includes a customization engine 164 that is configured to implement the techniques described herein. The customization engine 164 includes software processes, such as, for example, an onboarding process 130, a program development process 132, a program delivery process 134, and a learning process 136, among others. The content delivery service 120 may further include one or more data stores to store data such as user data database 124, content data database 126, and query data database 154 among other data. The data stores may be implemented using, for example, hard drives, solid state drives, or another form of non-volatile storage memory. The data stores may store their respective data in any suitable fashion such using a relational framework or a non-relational framework (e.g., key-value store, wide column store, document store, graph database, etc.).

The server computers 122 on which the processes execute may be computing devices that include one or more processors capable of executing program instructions and memory for storing the program instructions. The server computers 122 and the data stores may, for example, be housed in a data center and/or provided as a service from a data center. Alternatively or additionally, the server computers 122 and the data stores may be housed in a network operated and controlled by the content delivery service 120.

The onboarding process 130 may be activated when a new user is added to the content delivery service 120. The content delivery service 120 may detect a new user, for example, when the user launches the delivery application 112 for the first time. In these and other examples, the content delivery service 120 may launch the onboarding process 130. The onboarding process 130 may transmit to the delivery application 112 a series of questions, which are displayed to the user with prompts for answers. The user's responses may be transmitted back to the onboarding process 130, which may store the answers, with a user identifier, in the data store for the user data database 124. In some examples, the onboarding process 130 may also request, through the delivery application 112, for the new user to register with the content delivery service 120 and generate an account.

The content delivery service 120 may launch the program development process 132 once the onboarding process 130 completes. The program development process 132 may read the user's responses from the user data database 124, and determine a program of content for the user. Determining the program may include, for example, determining a score for each of a set of drivers. While a driver may describe a behavior or mode of thinking that underlies a psychological disorder, in the context of the content delivery system 100, a driver is a category for a set of content sessions. For example, a driver defined as a tendency to catastrophize may be associated with a content sessions that present techniques for coping with or correcting the tendency. In various examples, different drivers may be associated with the same or with different content sessions. Content sessions may also be referred to herein as atomic units, or atomic units of content.

Using the driver scores, the program development process 132 can generate a program of content for the user. Generating the program can include, for example, selecting individual content sessions that are associated with the drivers, where the content sessions can be selected based on the driver scores. For example, content sessions associated with drivers that have high scores will be selected, while content session associated with drivers that have low scores will not be selected. Generating the content program can further include determining an order in which to present the content sessions. For example, content sessions associated with the same driver may have a pre-defined order (e.g., the content sessions provide exercises that have a sequential order). As a further example, drivers that have scores that are similar (e.g., the difference is within a minimum threshold) may indicate that content sessions associated with these drivers should be inter-mixed. Generating the content program can further include determining when a user should be presented with the content. For example, the program development process 132 may determine that the user should be provided content sessions twice a day, once a day, once every other day, and/or whenever the user desires to consume the content. The program development process 132 can store the user's content program with the user's other data, in the data store for the user data database 124.

The program delivery process 134 can manage the delivery of the user's content program to the computing device 110. To do so, the program delivery process 134 can read form the user data database 124 the user's program, and determine the next content session to be presented to the user. The program delivery process 134 can then obtain the content from the data store storing the content data database 126, and transmit the content to the computing device 110. In various examples, the program delivery process 134 can further determine whether the user is following the schedule of delivery for content program. In these examples, the program delivery process 134 can push content to the delivery application 112 when the user is behind schedule, and/or can withhold content when the user is ahead of schedule.

The content delivery service 120 can use the learning process 136 to learn about the user. For example, the learning process 136 can keep track of the user's response to prompts that occur during the presentation of content. As a further example, the learning process 136 can keep track of how frequently the user uses the delivery application 112, whether the user maintains the schedule determined for the content program, and/or whether the user requests additional content, among other information. In various examples, the learning process 136 can aggregate user data from some or all of the users of the content delivery service 120, and use this information to modify the onboarding process 130, the program development process 132, the program delivery process 134, and/or the content sessions.

In some examples, the learning process 136 can also obtain data from a data service 152. In various examples, the data service 152 can obtain data about the computing device 110, such as location data determined by location devices 116 and data on the usage of applications 118 executing on the computing device 110. In various examples, the learning process 136 can use the data obtained from the data service 152 drive the program delivery process 134. For example, the program delivery process 134 may change the a user's content program and/or the content program's delivery schedule based on location data obtained from the computing device 110. The learning process 136 can further add the data from the data service 152 to the aggregate of data about the content delivery service's users, to further improve on the operation of the onboarding process 130, the program development process 132, the program delivery process 134, and the content sessions.

Figure 2:
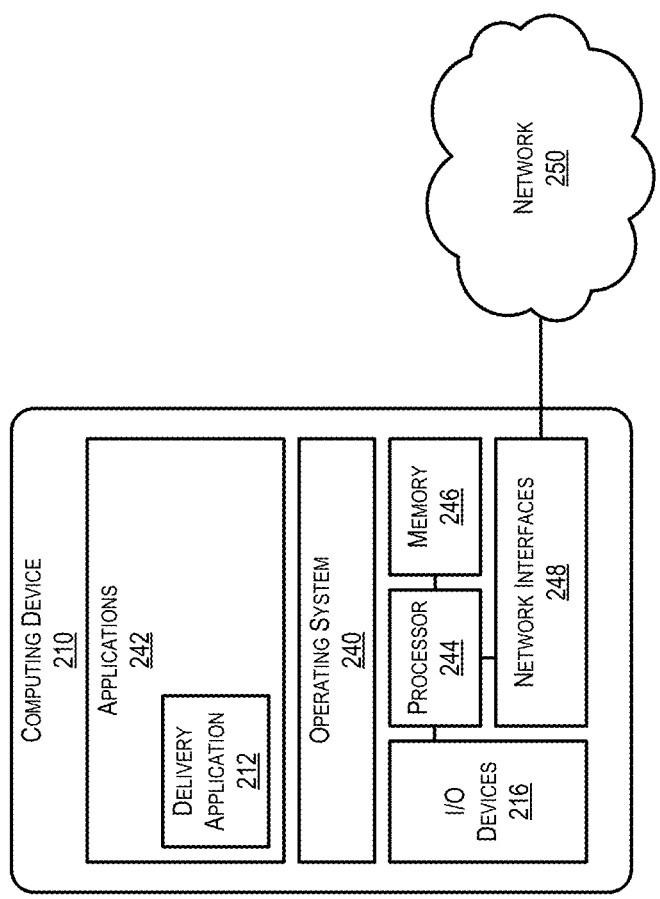
FIG. 2 includes an example block diagram illustrating an example of a computing device that may be used to implement techniques relating to generating and transmitting customized programs of content to computing devices, according to at least one example.

FIG. 2 includes an example block diagram illustrating an example of a computing device 210, such as the computing device illustrated in FIG. 1, that may be used to implement techniques relating to generating and transmitting customized programs of content to computing devices, according to at least one example. The example computing device 210 of FIG. 2 may include various hardware components and software components, which can be used in various combinations to present content to a user of the computing device 210. The content can include content sessions for CBT provided by a content delivery service.

In various examples, the software components can include an operating system 240 and applications 242. The operating system 240 can manage the various operations of the computing device 210, including the applications 242 executing on the computing device 210 and the computing device's hardware. The applications 242 can include programs accessible to a user of the computing device 210, including a delivery application 212, through which the user can interact with the content delivery service.

In various examples, the hardware components can include a processor 244, memory 246, Input/Output (I/O) devices 216, and network interfaces 248, among other components. The processor 244 can be an integrated circuit device that is operable to execute program instructions, including the instructions for executing the operating system 240 and the applications 242. The memory 246 can store the program instructions while the processor 244 is executing the instructions, and/or while the computing device 210 is powered off. In various examples, the computing device 210 can include multiple memories, including volatile and/or non-volatile memories. Non-volatile memories can also be described as non-transitory. The I/O devices 216 can include user input and output devices, such as display screens, touch screens, keyboards, mice, and so on. The I/O devices 216 can further include location devices, such as a Global Positioning System (GPS) receiver. The network interfaces 248 can include wired and/or wireless network devices, such as a network port, a Wi-Fi antenna, and/or cellular antennas, among other examples. The network interfaces 248 can enable the computing device 210 to communicate with a network 250, including, for example, the Internet.

Figure 3:
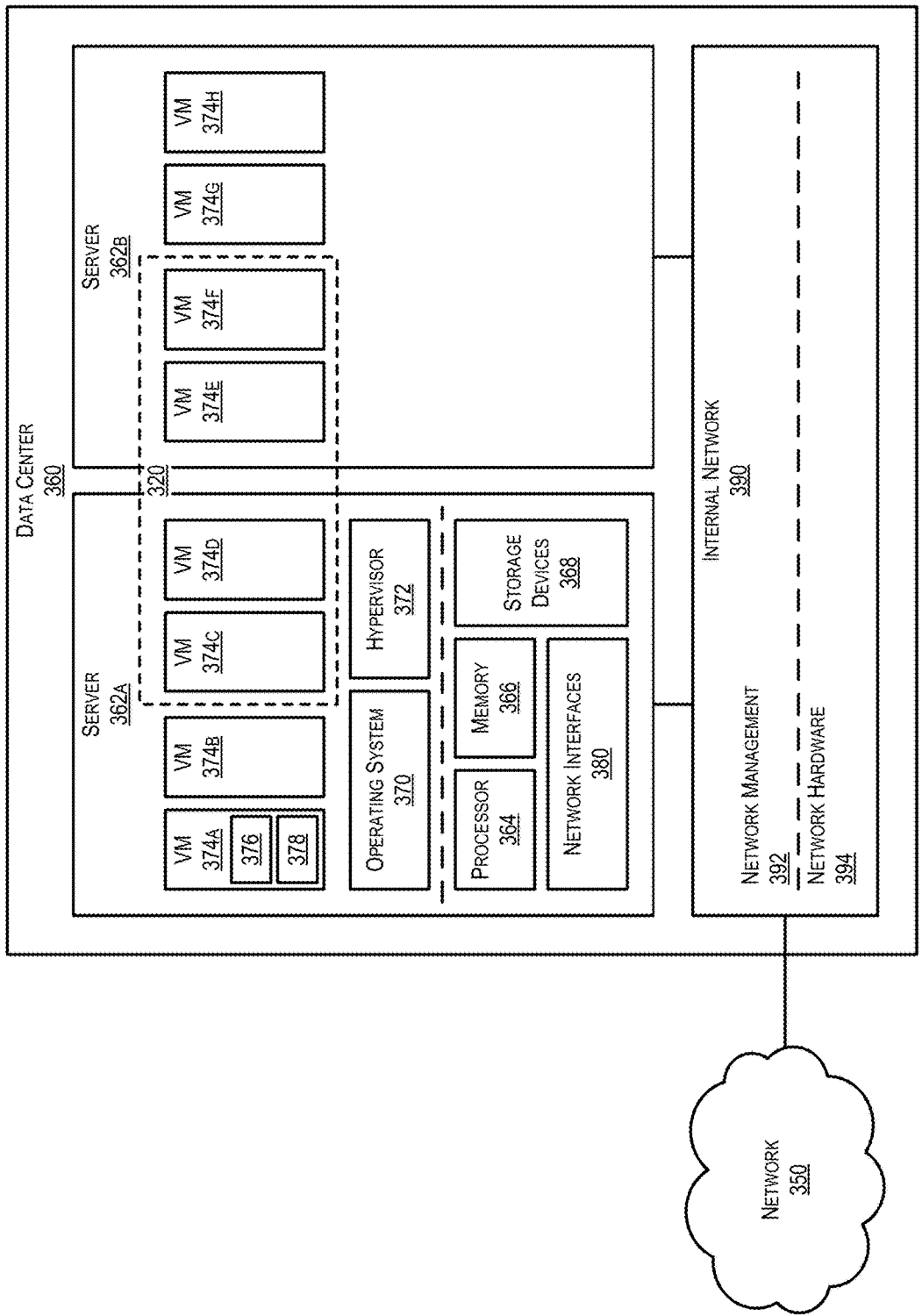
FIG. 3 includes a block diagram illustrating an example of a data center that may be used to implement techniques relating to generating and transmitting customized programs of content to computing devices, according to at least one example.

FIG. 3 includes a block diagram illustrating an example of a data center 360 that may be used to implement techniques relating to generating and transmitting customized programs of content to computing devices, according to at least one example. The data center 360 may host a content delivery service 320, such as the content delivery service illustrated in FIG. 1. The data center 360 may be operated by an entity other that the entity that controls the content delivery service 320, and may be leasing resources to the operator of the content delivery service 320. Alternatively, the data center 360 may be operated by the entity that controls the content delivery service 320.

The data center 360 may include multiple servers 362a-362b, of which two are illustrated here. A server may be a computing device configured primarily for being accessed over a network, and possibly for simultaneous use by multiple, unrelated users. An example of a configuration of a server is illustrated by a first server 362a in FIG. 3. As illustrated by the first server 362a, a server may include a software layer and a hardware layer.

The software layer may include, for example, an operating system 370 a hypervisor 372, and virtual machines 374a-374d, among other software and applications. The operating system 370 may control and coordinate the operations of the first server 362a, including execution of the hypervisor 372, the virtual machines 374a-374d, and operation of the hardware. The hypervisor 372, which may also be referred to as a kernel-based virtual machine (KVM) or a virtual machine monitor (VMM), may manage the virtual machines 374a-374d. For example, the hypervisor 372 may handle operations such as bringing up new virtual machines, use of the virtual machines of the first server's hardware, and taking down virtual machines, among other operations. In some examples, the hypervisor 372 is integrated into the operating system 370.

A virtual machine is an emulated computer system running on the hardware of a physical computer system. As illustrated by a first virtual machine 374a, a virtual machine may include a virtual representation of computer hardware 378, which may but need not map to the physical hardware of the computing system on which the virtual machine is running. The virtual machine may further include software 376 that is running on top of the virtual hardware 378. The software 376 may include an operating system and applications that are separate and distinct from the operating system 370 and applications of the first server 362a. As with physical computing systems, virtual machines may be isolated from one another, and a user operating within one virtual machine may be unaware of the existence of other virtual machines on the same system. The virtual machines 374a-374h illustrated in FIG. 3 may each have a similar configuration as is illustrated for the first virtual machine 374a, with variations in the software executed and/or the particular configuration of the virtual hardware.

The hardware layer of the example first server 362a may include a processor 364, memory 366, storage devices 368, and a network interface 380, among other hardware. The processor 364 is an integrated circuit device operable to execute program instructions, including the instructions for the programs executing in the software layer of the first server 362a. In some examples, the first server 362a may include multiple processors. In some examples, a processor may include multiple processing cores. While the processor 364 is executing program instructions, the program instructions may be stored in the memory 366. In various examples, the memory 366 may be volatile memory and/or non-volatile memory. In various examples, the first server 362a may include multiple different memories. The storage devices 368 may include non-volatile storage systems, such as hard drives, flash drives, and/or solid state drives, among other examples. While not being executed, and, in some cases, while being executed, program instructions may be stored on the storage devices 368. The memory 366 and the storage devices 368 illustrate two examples of non-transitory computer-readable mediums. The network interfaces 380 may include hardware and software for connecting the first server 362a to a network, such as the internal network 390 of the data center 360. In some examples, the first server 362a may include multiple network interfaces 380 so that the first server 362a may maintain multiple connections to the internal network 390.

In various examples, other servers in the data center 360, such as a second server 362b, may be configured similarly to the first server 362a, possibly with variations in the software being executed, the number of virtual machines running at any given time, and/or variations in the hardware included in the server.

The internal network 390 of the data center 360 may connect the servers 362a-362b of the data center 360 to each other and to external networks 350, such as the Internet. The internal network 390 may include network management 392 software, which may perform operations such as balancing the workload on each of the servers 362a-362b, bringing up and taking down servers, and/or assigning the data center's users to servers and/or virtual machines on the servers, among other operations. The internal network 390 may further include network hardware 394, such as the routers, switches, hubs, and gateways that form the internal network 390.

A user of the data center 360 may include the content delivery service 320. The content delivery service 320 can, for example, be assigned one or more virtual machines in the data center 360, which the content delivery service 320 may use for executing the various processes of the content delivery service 320. The data center 360 may be configured such that the operator of the content delivery service 320 need not know where the virtual machines assigned to the content delivery service 320 are executing. In the example of FIG. 3, the content delivery service 320 has been assigned several virtual machines executing on the first server 362a and several executing on the second server 362b. In various examples, the data center 360 may determine to move the content delivery service 320 to different servers, and may thus migrate the operations of the content delivery service 320 from one virtual machine to another.

In various examples, the operator of the content delivery service 320 may access the virtual machines assigned to the content delivery service 320 from the network 350. For example, the data center 360 may provide a console or graphical user interface through which the operator may configure the virtual machines. In various examples, the data of the content delivery service 320 may be stored on the storage devices 368 of the servers, and/or on network attached storage devices in the data center 360.

The services of the content delivery service 320 may further be provided over the network 350 to users. For example, the virtual machines assigned to the content delivery service 320 may each include a virtual network interface, through which the virtual machines may communicate with the network 350. Communications may include receiving input from user devices and/or transmitting content to the user devices.

A multimedia content delivery system may be used to deliver content that teaches CBT techniques. CBT is a mental health method that focuses on challenging and changing unhelpful cognitive distortions (e.g., thoughts, beliefs, and attitudes, for example) and behaviors, improving emotional regulation, and the development of personal coping strategies that target solving problems. Cognitive behavioral therapy has historically been delivered by authorized professionals, and is a widely accepted psychiatric method for certain psychological disorders.

There exist limitations in the current delivery of CBT. For example, treatment tends to focus on determining a user's finding (e.g., diagnosis), and determining a treatment based on the finding. For example, a user found with anxiety may be given a regimen for anxiety, while the user may be suffering from both anxiety and insomnia, in varying degrees. As another example, CBT focuses on thoughts and behaviors, which may need to be dealt with at any point in time during a user's day. In most cases, a user may not have any-time access to a special, and thus may lack the necessary guidance when the guidance is needed.

In various implementations, provided is a content delivery system that provides content sessions for CBT. In various examples, well-established and widely used CBT techniques may be captured in digital multimedia presentations. Individual steps in the overall therapy regimen may be divided into sessions of content, with each session including a digital multimedia presentation. In some examples, a content session may be interactive, with prompts presented to the user and a the content of the session being response to the user's inputs. In various examples, the sessions of content may be delivered through an application executing on a user's computing device. A digital, computerized CBT delivery system may enable CBT to be available on an anytime, anywhere basis, thus reducing or eliminating the need for a human therapist.

Computer-driven delivery of CBT may further be customized for each user, and the customization may focus on the user's issues, rather than the user's finding. For example, the content delivery system may be configured to determine a user's drivers (e.g., the factors that underlie the user's psychological issues) and use the drivers not to determine a finding, but rather to determine a program of content for the user. Determination of the drivers uses standardized techniques for identifying psychological disorders, however, the content delivery system takes the approach that different, recognized disorders may have the same drivers. This transdiagnostic approach to CBT may provide better user experiences, and better treatment results.

The techniques described herein constitute one or more technical improvements to the systems and devices on which the techniques are performed. For example, physical storage medium space along with bandwidth are conserved because the content is managed at a central location (e.g., the content delivery service) and shared on-demand and in a customized manner to the computing device. Thus, unlike conventional self-help applications that provide the same content irrespective of user characteristics, the techniques for customization described herein may provide the data that is needed for the customized program of content. Additionally, because the programs of content are generated using vetted CBT approaches, users are able to successfully complete CBT much more efficiently that using conventional in-person sessions.

Figure 4:
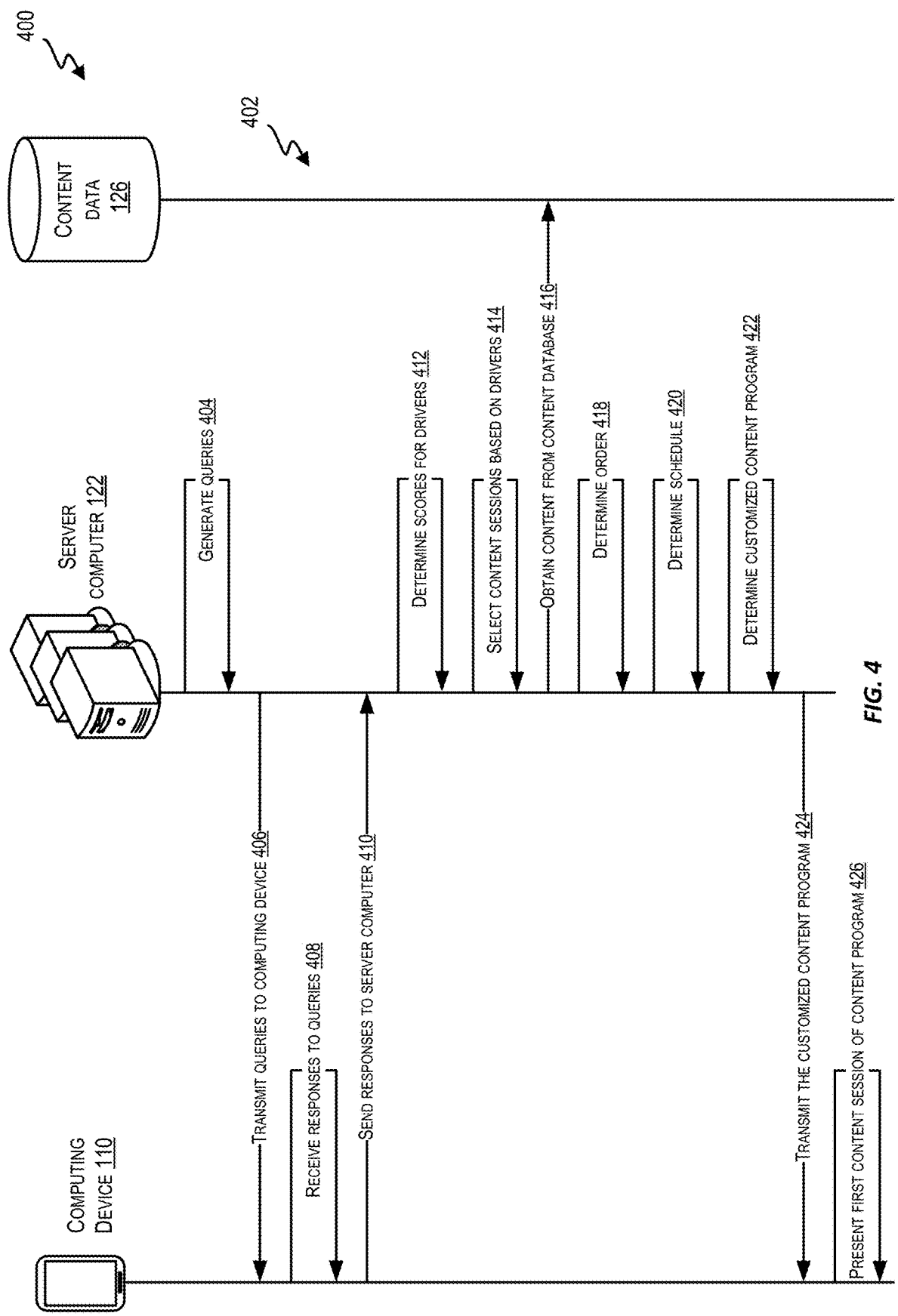
FIG. 4 includes a diagram illustrating example functions of elements of a computer system that may be used to implement techniques relating to generating and transmitting customized programs of content to computing devices, according to at least one example.

FIG. 4 includes a diagram illustrating example functions of elements of a computer system 400 that may be used to implement techniques relating to generating and transmitting customized programs of content to computing devices, according to at least one example. The computer system 400 includes the computing device 110, the server computer 122, and the content data database 126. In the system 400, each of these elements is illustrated as performing at least one part of a process 402 for determining and transmitting a customized content program.

The process 402 begins at 404 by the server computer 122 generating queries. This may include the server computer 122 reading the queries from a database such as the query data database 154. In some examples, the server computer 122 may generate the queries based on queries suitable for identifying a psychological issue, suitable for assisting a user to describe her psychological issue using her own words, and any other type of query. In some examples, the server computer 122 may generate the queries based on information about a user of the computing device 110. For example, prior to generating the queries, the server computer 122 may obtain or otherwise access contextual information (e.g., demographic, location, etc.) about the user and use this information for generating a set of queries that is customized to the user.

A first set of queries from the series of queries may be for screening for psychological issues. The computing device 110 may display the series of queries in an application executing on the computing device 110. Each query may further be displayed with a prompt for an response. In some examples, the first set of queries are derived from researched psychological screening questionnaires. For example, the queries may be selected from questionnaires most commonly used for screen for disorders such as anxiety, depression, or insomnia, among other examples. Queries taken from screening questionnaires are generally presented verbatim, to ensure that the diagnostic purpose of the query is maintained.

In some examples, a second set of queries from the series of queries may be for determining a manner in which a user frames the user's particular psychological issues. The queries in the second set of queries may be derived from screening questionnaires, however, these queries may be modified so that the user's understanding of the user's problems may be determined. For example, the queries in the second set may be asking or the same information (e.g., is the user experiencing anxiety), but may use different phrasing or wording, so that the phrases or words the user uses may be determined.

In some examples, a third set of queries from the series of queries may be for relating to a user. These queries may be derived from studies, but may be selected more for showing empathy than for diagnostic purposes. Examples of such queries include, "Have you had a bad day?" "Do you need to talk to someone?" or "Do you need to take a few minutes for yourself?" among other examples.

At 406, the process 402 includes the server computer 122 transmitting the queries to the computer device 110 such as via a network. In some examples, this may include transmitting the queries responsive to a trigger, such as the user opening an application on the computing device 110.

In some examples, the server computer 122 may organize the queries into a graph structure such as a decision tree. In these examples, the graph enables the delivery application to change the queries that are presented to the user based on the user's answers. For example, if a user responds "no" to the query "Do you have trouble falling asleep at night?" the series of queries may exclude the portion of the graph that includes queries about insomnia, and may instead take a different direction. As another example, if the user answers "yes" to the query "Do you think you worry a lot?" then the delivery application may start asking queries from the part of the graph that includes queries about anxiety. Using a graph structure also enables the line of questioning to be flexible. For example, if query about anxiety asks "Do your worries keep you up at night?" and the user answers yes, then the delivery application may return to queries about insomnia.

At 408, the process 402 includes the computing device 110 receiving responses to the queries. In some examples, the user may use an input device to input responses to the queries. For example, the user may speak her responses, type her responses, select her responses from a set of multiple choices, etc. In some examples, the computing device 110 may also include the functionality to determine additional queries based on the responses.

At 410, the process 402 includes the computing device 110 sending the responses to the server computer 122 such as via a network. In some examples, the responses may be sent in batches or one at a time. As described herein, blocks 404-410 may be iteratively repeated, with block 404 generating new queries based on responses received from the computing device 110 at block 410. In some examples, the responses may be tagged or otherwise identified with the query for which the response was provided.

At 412, the process 402 includes the server computer 122 determining scores for drivers. In some examples, a driver is a factor underlying one or more psychological issues. A driver may be associated with one or more psychological disorders. For example, a same driver may both cause anxiety and insomnia. In the context of the content delivery service 120, the set of drivers is associated with a plurality of content sessions, where each content session includes a multimedia presentation related to CBT. The drivers may be used by the content delivery service 120 as classifications or categorizations for different content sessions. The content delivery service 120 can, for example, user four to five, or up to seven drivers, or possibly more.

In various examples, content sessions may be organized into programs, with each driver having one or more programs. A program or content program is a series of content sessions, in a particular order and on a certain schedule. The content sessions in the series may present, for example, steps in learning CBT techniques. Each content session may include content items that form a standalone presentation of audio, video, and/or still images, with a defined beginning and end. A content unit may be interactive, and thus request and respond to user input. The content sessions in a program may be on a schedule, such as in cases where the information being presented is best ingested within certain time periods (e.g., twice a day initially, then once a day after a week, and then once a week after several more weeks, as one example). Alternatively or additionally, some programs or parts of a program may not include a specific schedule, so that the user may determine when to ingest a particular content session.

In various examples, one driver may be associated with more than one content program. For example, the content delivery service 120 may have different programs for different score values for the driver. For example, when the score for a driver is at least 30 out of 100, then the content delivery service 120 may select a first program, when the score is at least 50 the content delivery service may select a second program, and when the score is over 70, the content delivery service may select a third program. These different programs may reflect, for example, different approaches to a CBT technique, which may address differing intensity of people's issues. Alternatively or additionally, the content delivery service 120 may have different content programs for the same driver that are selected based on the scores of multiple drivers. For example, when a first driver has a score of 50 and a second driver has a score of 30, the content delivery service may select a different program from among programs associated with the first driver, than when the second driver has a score of 0.

To determine a score for a driver, in various examples, the content delivery service 120 may compute a weighted sum of the user's answers to the queries. Some queries may be related to a specific driver, while some queries may be related to several drivers. As an example, for a multiple choice question, a response of choice A may be given a weight of 0.75 out of 1, response choice B may be given a weight of 0.2, response choice C may be given a weight of 0.05, and response choice D may be given a weight of 0 with respect to a first driver. Additionally, in this example, choice A may be given a weight of 0, choice B a weight of 0.1, choice C a weight of 0.3, and choice D a weight of 0.6 with respect to a second driver. In various examples, the assignment of weights may be based on the content and intent of each query. Some queries, such as queries to gain information about the user, may not be specifically related to drivers, and thus may not be included in computation of the driver score.

At 414, the process 402 includes the server computer 122 selecting content sessions based on the drivers. For example, the process 402 may include determining a first driver from the set of drivers that has a highest score, and selecting a particular content program from a plurality of content programs associated with the first driver. The process 402 may then include using the particular content program to select the particular content sessions, and using the particular content program to determine the order and the schedule. As another example, the process 402 may include determining a first driver from the set of drivers that has a highest score and determining a second driver from the set of drivers that has a second highest score. In this example, the content sessions may be selected from a first content program associated with the first driver and a second content program associated with the second driver. In this example, in some cases all of the content sessions from the first content program and the second content program may be included among the selected content session. In some cases, some content sessions may be omitted, such as content sessions that are similar or have overlapping information. Alternatively or additionally, some content sessions may be omitted for not being sufficiently relevant to the user, which may be determined from the driver scores.

In various examples, thresholds may be used to determine whether content sessions associated with a particular driver should be selected. For example, when a driver score is less than a threshold of 25, then the server computer 122 may determine not to include content sessions associated with the driver in the pool of content from which to select sessions. As another example, when a driver score is between the thresholds of 25 and 50, the server computer 122 may give content sessions associated the driver secondary consideration. As another example, when a driver score is between the thresholds of 50 and 75, the server computer 122 may give the content sessions associated with the driver primary consideration. As another example, when a driver score is above a threshold of 75, the server computer 122 may give content sessions associated with the driver primary consideration, and may push content sessions for other drivers into a pool that is given tertiary consideration. In these examples, the server computer 122 may select from among primary content session first, and select from among secondary and tertiary content sessions if, for example, some of the content sessions would be augmented by sessions from the secondary or tertiary pool, or for other reasons.

At 416, the process 402 includes the server computer 122 obtaining content from the content data database 126. This may include obtaining the actual content that will be used to populate the content sessions determined at block 414. In some examples, the content in the content database 126 may be indexed using tags associated with the content sessions and/or drivers such that obtaining the content at 416 includes querying the database 126 using tags.

At 418, the process 402 includes the server computer 122 determining an order of the content sessions. At 420, the process 402 includes the server computer 122 determining a schedule for the content sessions. The order and the schedule may be based on the scores and drivers associated with the content sessions. The content sessions, the order, and the schedule for presenting the content sessions may constitute a customized content program. The order is the order in which to present the content sessions. In various examples, content sessions associated with higher-scoring drivers may be presented before content sessions associated with lower-scoring drivers. For example, content sessions from the first content program may be given higher priority in the order than content sessions from the second content program, due to a driver associated with the first content program having a higher score than a driver associated with the second content program. In some cases, the content sessions from different programs may be intermixed, so that, for example, a content session from a first content program is followed by two content session from a second content program, among other examples.

The schedule may include days or times when each content session from the content sessions is to be delivered. In various examples, the schedule may be determined from the driver scores. For example, the schedule be more condensed and/or frequent when a driver score is higher, so that the user ingests some of the content sessions over a shorter period of time. As another example, the schedule may be more spread out and infrequent when the driver score is higher.

At 422, the process 402 includes the server computer 122 determining a customized content program. As described herein, determining the customized content program may be based on blocks 414, 418, and 420.

At 424, the process 402 includes the server computer 122 transmitting the customized content program. In some examples, the server computer 122 may transmit the customized content program to the computing device 110. In some examples, the process 402 may include transmitting the content program to the computing device 110 according to the order and the schedule. In some examples, the delivery application may prompt the user when the schedule indicates that the user is to ingest the next content session. In some examples, the delivery application may determine the user's next content session whenever the user launches the application. When the user launches the application and activates a content session, the delivery application may request the data for the content session from the server computer 122, which may then transmit the data to the user's device.

At 426, the process 402 includes the computing device 110 presenting a first content session of the customized content program. This may include the delivery application determining the first content session based on information received from the server computer 122 at block 424. The computing device 110 may then use the order and schedule to determine when to present additional sessions.

In some examples, the process 402 may further include receiving, from the computing device 110, data corresponding to user input into the application. The data may include, for example, a record of each occurrence of the application being launched. Keeping track of when the user launches the delivery application may be useful in determining whether the user is engaging with the service in a consistent fashion and/or according to the schedule of the user's content program. The data, alternatively or additionally, may include a response to a query presented when the application is launched. For example, the delivery application may present the user with a query such as "How are you doing today?" when the delivery application is launched, and may send the user's response to the server computer 122. As another example, the delivery application present a more personalized question, such as "What is your anxiety level today?" The data can, alternatively or additionally, include a comparison of when the particular content sessions were output by the application to the schedule of the content program. For example, the user may be ahead of the schedule or may be falling behind the schedule. In this example, the delivery application may report to the server computer 122 whether and to what degree the user is on or off schedule.

In some examples, the process 402 may further include modifying, based on the data, the particular content sessions included in the customized content program. For example, the server computer 122 may determine to add or remove content session from the program. In some examples, the process 402 may include adjusting, based on the data, the order or the schedule of the particular content sessions. For example, the server computer 122 may swap a content session that is later in the order for a content session that is earlier in the order. As another example, the data may indicate that the user is responding well to content sessions that the user has so far ingested, and that content sessions yet to be ingested may be presented on a longer schedule.

Figure 5:
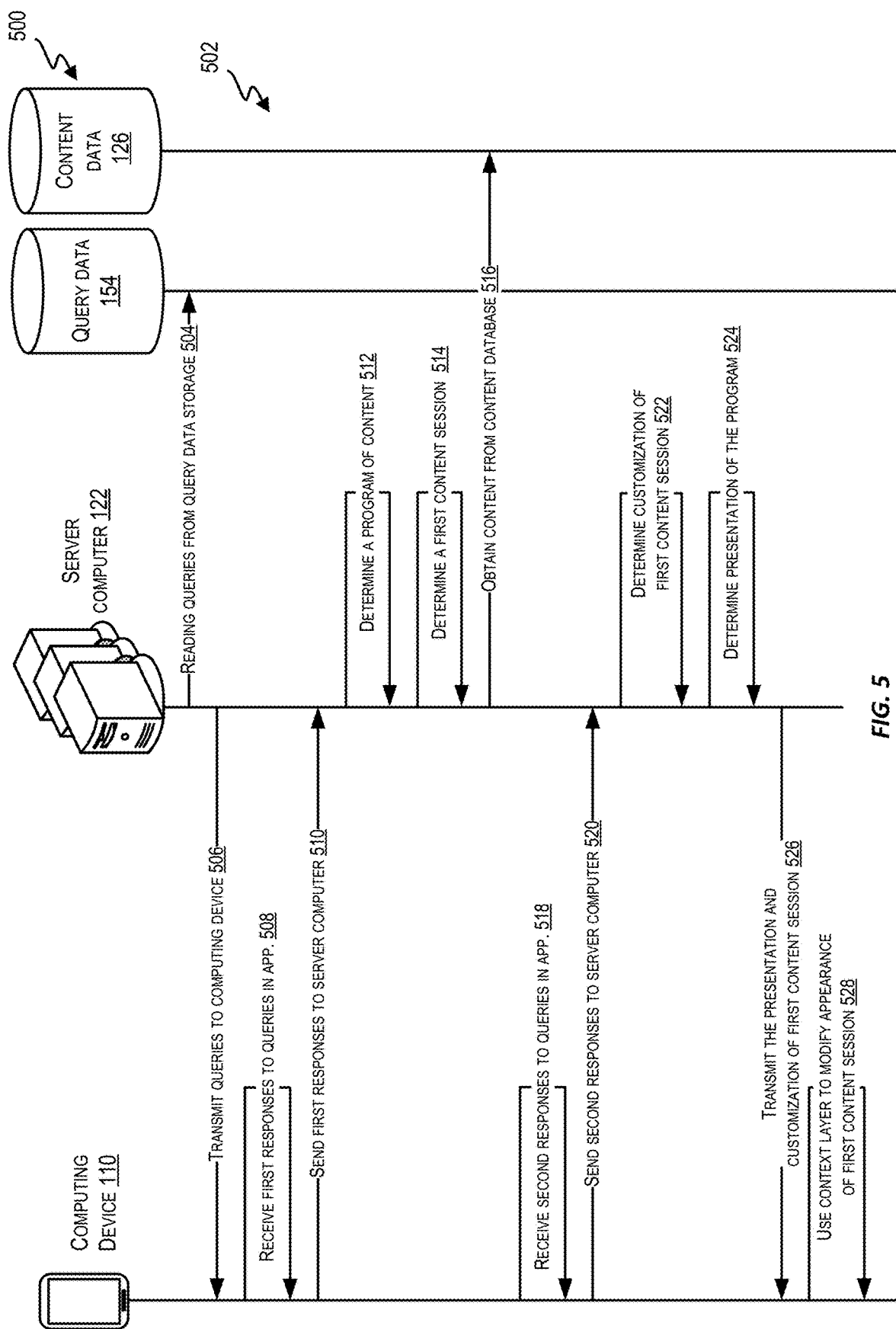
FIG. 5 includes a diagram illustrating example functions of elements of a computer system that may be used to implement techniques relating to generating and transmitting customized programs of content to computing devices, according to at least one example.

FIG. 5 includes a diagram illustrating example functions of elements of a computer system 500 that may be used to implement techniques relating to generating and transmitting customized programs of content to computing devices, according to at least one example.

The computer system 500 includes the computing device 110, the server computer 122, the content data database 126, and the query data database 154. In the computer system 500, each of these elements is illustrated as performing at least one part of a process 502 for determining and transmitting a presentation and customization of a content program to the computer device 110.

The process 502 begins at 504 by the server computer 122 reading queries such as a series of queries from query data storage such as the query data database 154. In some examples, the query data database 154 may be associated with the server computer 122, as described with respect to FIG. 2. A first set of queries from the series of queries can be for screening for psychological issues. As described with respect to FIG. 4, in some examples, the first set of queries is derived from researched psychological screening questionnaires, a second set of queries from the series of queries can be for determining a manner in which a user frames the user's particular psychological issues, and a third set of queries from the series of queries can be for relating to a user.

At 506, the process 502 includes the server computer 122 transmitting the queries to the computing device 110 such as via a network. Block 506 may be performed in a similar manner as described with reference to block 406. In some examples, the computing device 110 can display the series of queries in an application executing on the computing device 110. The queries can be displayed sequentially, with a new query being displayed once a response is provided to a currently-displayed query. Each query can be displayed with a prompt for a response.

At 508, the process 502 includes the computing device 110 receiving first responses to the queries in the application executing on the computer device 110. Block 508 may be performed in a similar manner as described with reference to block 408.

At 510, the process 502 includes the computing device 110 sending first responses to the server computer 122 such as via a network. In some examples, the first responses constitute a portion of the queries sent to the computing device 110 at 506. Block 510 may be performed in a similar manner as described with reference to block 510.

At 512, the process 502 includes the server computer 122 determining a program of content. This may include the server computer 122 computing scores for drivers associated with the queries based on the responses. Block 512 may include sub-blocks similar to blocks 412 and 414.

At 514, the process 502 includes the server computer 122 determining a first content session. The first content session may be the first session in the program of content. In some examples, the server computer 122 may determine the first content session based on scores for drivers and based on the program of content.

At 516, the process 502 includes the server computer 122 obtaining content from the content database 126. Block 516 may be performed in a similar manner as described with reference to block 416. The content may be used to populate the program of content.

At 518, the process 502 includes the computing device 110 receiving second responses to the queries in the application. The second responses may correspond to a second set of queries of a different query type than the first responses. In some examples, the block 518 may be performed in a similar manner as described with reference to block 508.

At 520, the process 502 includes the computing device 110 sending second responses to the server computer 122. Block 520 may be performed in a similar manner as described with reference to block 510. In some examples, the second responses may be received by the server computer 122 prior to server computer determining the program of content. In some examples, the first responses relate to the program of content and the second responses relate to the particular content of the sessions. For example, the first responses may indicate that the user has drivers relating to depression and anxiety. These responses may be used to build a program of content that includes content sessions to address depression and anxiety. The second responses may indicate that the user would respond to one type of content (e.g., interactive modules) better than a second type of content (e.g., video or audio). Using the responses to different types of queries, the server computer 122 may build a profile of the user that includes her preferences, her drivers, and other information about the user. The profile may be saved in the user data database 124, and referenced when building programs of content and customizations.

In some examples, queries are stored on the storage device in a graph structure. In these examples, queries can each be associated with a node in a graph, and responses to the queries can each be represented by a path to another node. In these examples, the queries to which the second responses are directed may have been determined by the computing device 110 and/or the server computer 122.

At 522, the process 502 includes the server computer 122 determining a customization of the first content session. This may include the server computer 122 using the second responses to determine the customization. In some examples, the customization may include tailoring the content of the first content session based on inferred, learned, or otherwise known information about the user. For example, certain content items of the first content session may be removed, while others are added. In some examples, the customization may be based on the first responses and/or the second responses. Each content session may include a multimedia presentation related to CBT. For example, the content sessions can be steps in teaching a CBT technique. In some cases, a content session can be interactive, so that the delivery application prompts the user for input and the content session reacts to the input. By being based on the responses to the questions, the program of content can be customized to a particular user.

At 524, the process 502 includes the server computer 122 determining a presentation of the program of content. In some examples, the presentation may include graphics, text, and audio. In some examples, text or audio of the presentation may include words that a user indicated, in the first set of responses or the second set of responses, as describing the user's psychological issues. For example, the user can be presented with a series of queries that each seek a response to the query "Do you have anxiety" but that use different phrases to describe the concept, such as "Do you feel stressed out all the time?" or "Are you constantly afraid of the worst thing happening?" or "Do you feel stuck in your head all the time?" among other examples. The query to which the user responded "yes" can then be used as the basis for text and/or audio used when a content sessions is played.

At 526, the process 502 includes the server computer 122 transmitting the presentation and the customization of the first content session to the computing device 110 such as via a network. Block 526 may be performed in a similar manner as block 424.

At 528, the process 502 includes the computing device 110 using a context layer of the application to modify an appearance of the first content session. The presentation can modify the appearance of the first content session without modifying information included in the first content session. For example, the first content session can include a video, and the presentation can modify the text displayed with the video or the audio output with the video. As another example, the presentation can change color schemes or graphics themes or background music, among other examples. In some examples, the presentation is further based on demographic information determined using the first responses and/or the second response. For example, the presentation can be different for younger adults than for older adults. in some examples, the presentation is further based on location information derived from the computing device 110. For example, the presentation can use different graphics themes on a computing device located in the far east versus one located in North America. In some examples, the customization may include adding the user's name to the content. For example, a particular portion of the first content session may begin by playing an audio recording that includes the user's name, such as "Hi, Isaac! Let's get started."

Figure 6:
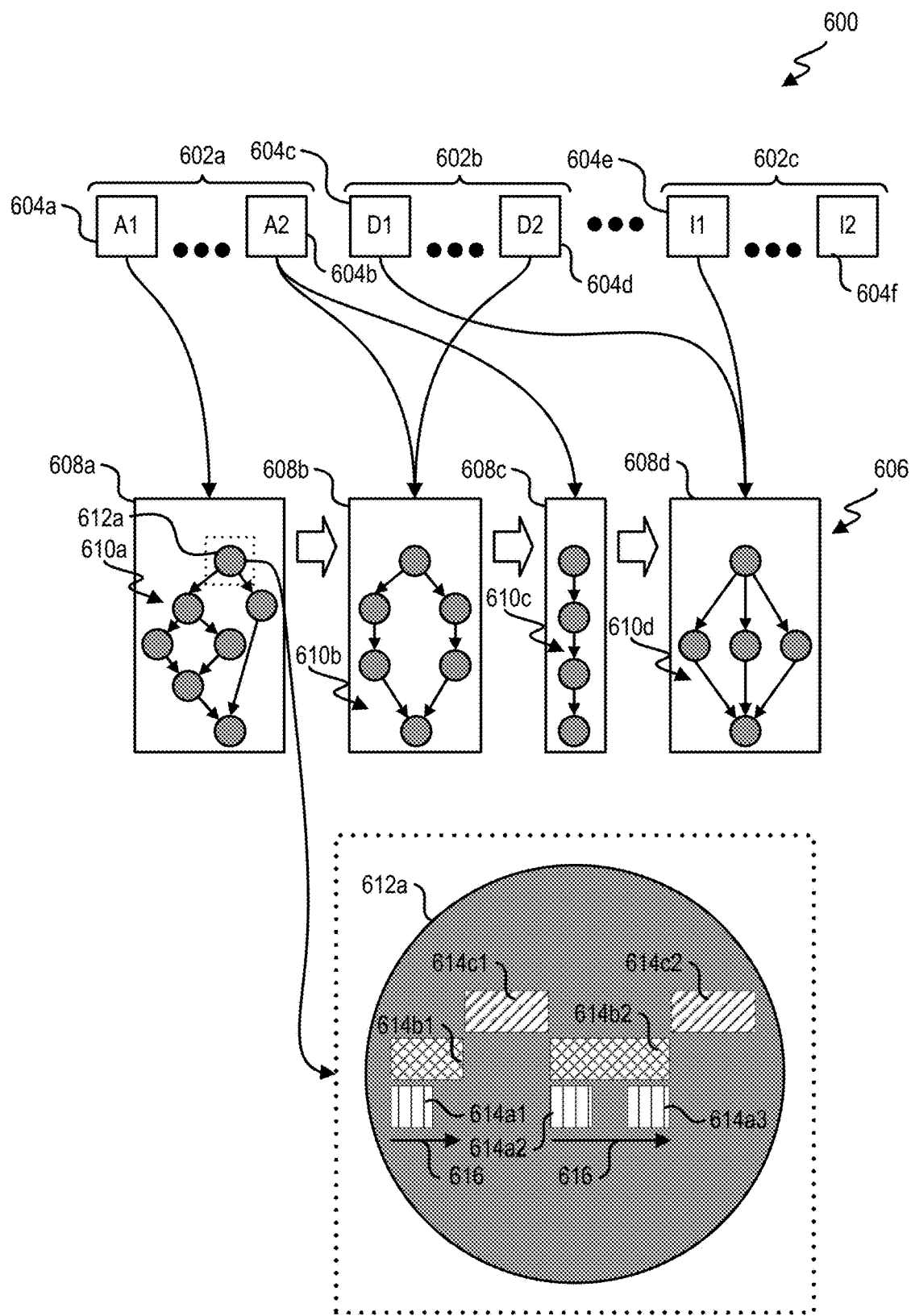
FIG. 6 includes a diagram illustrating aspects of a customized program of content, according to at least one example.

FIG. 6 includes a diagram 600 illustrating aspects of a customized program of content, according to at least one example. The diagram 600 includes a plurality of driver categories 602a-c. Each driver category 602 includes drivers 604 organized by a particular category of issue that can be addressed using a CBT technique. For example, the category 602a includes drivers 604a and 604b (i.e., A1 and A2) each associated with an aspect of anxiety. The category 602b includes drivers 604c and 604d (i.e., D1 and D2) each associated with an aspect of depression. The category 602c includes drivers 604e and 604f (i.e., I1 and I2) each associated with an aspect of insomnia. The ellipsis between individual elements, such as between the drivers 604 within each category 620 and between driver categories 602, are meant to illustrate that any suitable number of elements may be included in the set of elements. Thus, more than two drivers 604 may be included in each driver category 602, and more than three driver categories 602 may be provided (e.g., other categories relating to other psychological health issues such as stress, neurosis, mania, delirium, dementia, narcissism, paranoia, etc. may be included).

In some examples, users responses to the queries described herein may be used to select a set of drivers 604. For example, scores may be computed based on the user responses, and the scores may indicate which specific drivers among the different driver categories 602 are applicable to addressing the user's issue(s). Because the technology described herein is used to implement a transdiagnostic approach, the scores will often indicate drivers 604 from more than one category as being relevant to a particular user.

The set of drivers 604 in this example include 604a and 604b each relating to anxiety, 604d relating to depression, and 604e relating to insomnia. The set of drivers are used to build a program of content 606 including a plurality of content sessions 608a-608d. In this manner, the program of content 606 (e.g., which content sessions 608 are selected, how many, their order, and schedule) may be customized to a user.

In some examples, a driver 604 maps directly to a content session 608. For example, anytime an A1 driver (e.g., the driver 604a) is identified, the content session 608a may be selected. A content session 608 may also map to more than one driver 604, and a driver 604 may map to more than one content session. For example, a D1 driver (e.g., the driver 604c) and an I1 driver (e.g., the driver 604e) may map to the content session 608e. An A2 driver (e.g., the driver 604b) maps to the content sessions 608b and 608c. As illustrated, the mappings from drivers 604 to content sessions 608 may result in some content sessions that address drivers 604 from different driver categories 602.

Determining the program of content 606 may include collecting the relevant content sessions 608 based on the drivers 604 identified. In some examples, the order and schedule of the content sessions 608 within the program of content 606 may be determined based on the scores, the drivers 604 themselves, and/or any other suitable information (e.g., contextual information, either inferred or otherwise obtained from the user). For example, certain types of content sessions 608 may be more suitable for presentation at the beginning of the program of content 606 because their purpose is to introduce the user and/or prepare the user for additional content sessions 608. Information associated with the drivers 604 may, in some examples, indicate when a related content session 608 should be presented.

Each content session 608 includes a content graph 610. Each content graph 610, sometimes referred to a slide graph, includes one or more nodes 612 connected with branches. The content graphs 610 may be used to guide the user through the particular content of the content session 608. In some examples, depending on the user's reactions, responses, activity level, engagement level, responses to queries, and the like, different paths (e.g., from node to node) through the content sessions 608 may be developed. In some examples, the content graphs 610 are customized to a user based on the user's responses to the initial queries, contextual information, or other feedback from the user. For example, for a first user, the content graph 610b may include two branches, but for a second user, the content graph 610b may include one, three, or more branches. In this manner, each content session 608 within the program of content 606 may be customized to a user.

Each node 612 in each content graph 610 may include multiple content items 614 of various types. For example, a particular content node 612a of the content graph 610a (illustrated at the bottom of the diagram 600) is shown in detail as including a plurality of content items 614. Each of the other nodes 612 in each of the other content graphs 610 may also include one more content items 614.

Arrows 616, in the node 612a, represent that at least some content items 614 may include a time element, i.e., be presented in accordance with a timeline. For example, the content item 614a1, which represents an audio segment, and the content item 614b1, which represents a video segment, may overlap in time and constitute the initial content presented as part of the node 612a. The audio segment content item 614a1 may be spliced together with the video segment content item 614b1 to create a seamless presentation of audio and video content. In some examples, one or more of the content items 614 may be customized to the user. For example, the audio segment 614a1 may identify the user by her name (e.g., "Hi Laura, let's get going!"), while the video segment 614b1 displays a message relating to the content of the node 612a.

The node 612a also includes additional audio segment content items 614a2 and 614a3 which are time based and may be presented simultaneously with an additional video segment content item 614b2. The node 612a also includes content items 614c1 and 614c2 that are not time-based. For example, the node 614c1 represents an interactive module that may require some input from the user before completion. The interactive module content item 614c1 may test the user to establish a baseline or determine whether the user is progressing appropriately. The node 614c2 represents one or more queries that may be posited to the user regarding the content of the node 612.

The mappings and associations between the drivers 604 and the content sessions 608 may be stored in a database such as the query data database 154. The actual content that is used to populate the content sessions 608 may be stored in a different database such as the content data database 126. In some examples, the content data database 126 may be hosted by an entity other than the entity that hosts the content delivery service 120.

Figure 7:
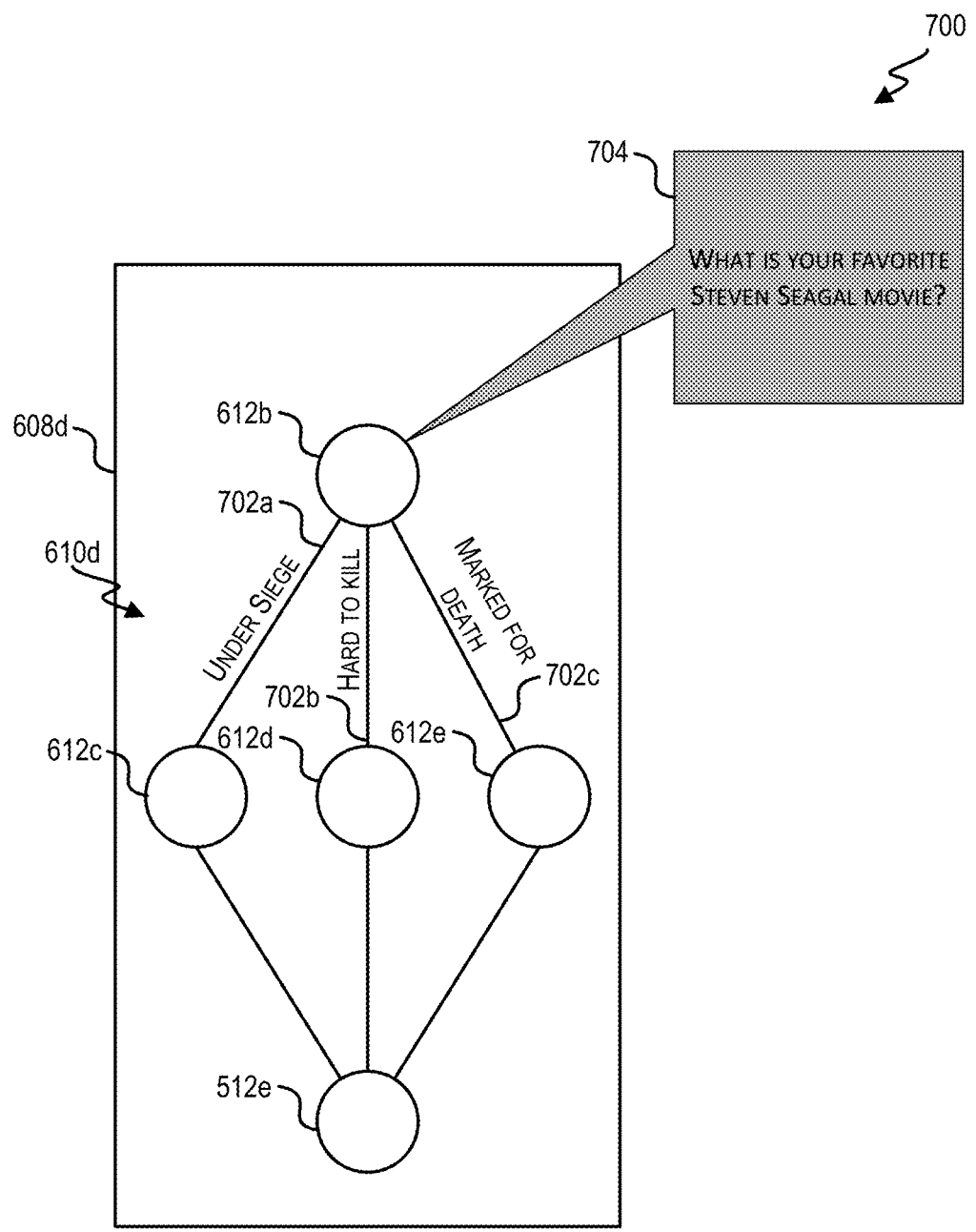
FIG. 7 includes a diagram illustrating aspects of a customized program of content, according to at least one example.

FIG. 7 includes a diagram 700 illustrating aspects of a customized program of content, according to at least one example. In particular, the diagram 700 includes the content session 608d. The content session 608d relates to a coaching questionnaire that uses a query 704 to traverse the content graph 610e. Thus, in this example, the first node 612b of the content graph 610e is used to present the query 704 to the user. The query 704 can be any suitable query. In this example, the query 704 is associated with multiple responses, represented by branches 702a-702c that connect the node 612a with respective nodes 612c-612e. Depending on which response the user selects, the content of selected respective node 612 will be presented.

Figure 8:
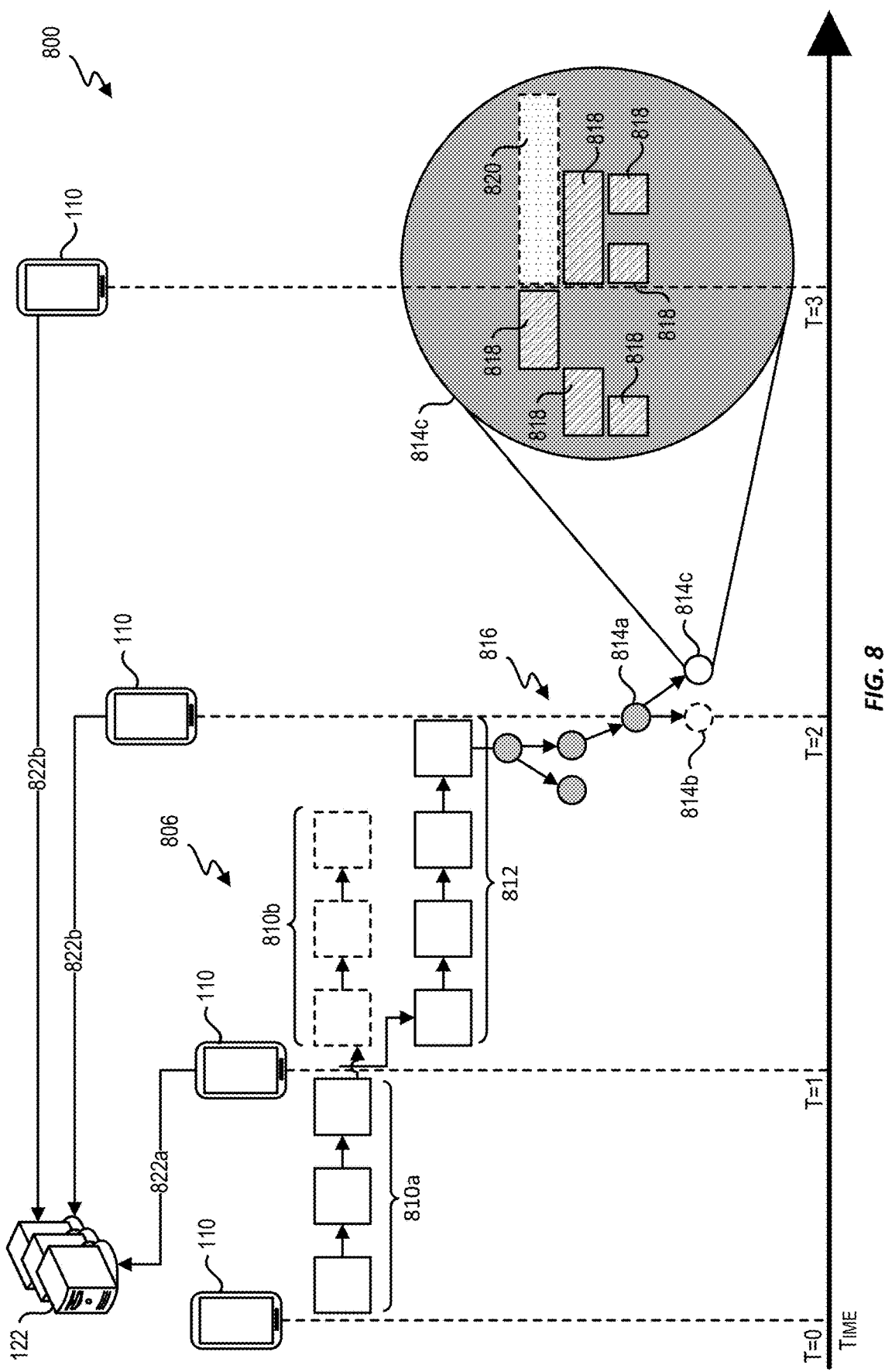
FIG. 8 includes a diagram illustrating aspects of dynamically customizing a program of content, according to at least one example.

FIG. 8 includes a diagram 800 illustrating aspects of dynamically customizing a program of content 806 (e.g., the program of content 606), according to at least one example. The diagram 800 in particular illustrates dynamically customizing the program of content 808 at three different times, T=1, T=2, and T=3 based on the same or different types of feedback. The program of content 808 was originally generated prior to T=0 using the techniques described herein, e.g., responses from users, computing scores for drivers, etc.

At T=0, the program of content 808 included six original content sessions, represented by original content session subset 810a and original content session subset 810b. These six original content sessions were originally customized to the user and it was expected that the user would complete all six sessions. Thus, at T=0, the first content session in the content session 810a is presented to the user at the computing device 110. Between T=0 and T=1, the user completes three content sessions, i.e., those in the content session subset 810a. But, at T=1, the computing device 110 provides feedback 822a to the server computer 122. The feedback can include passive feedback such as whether the user engages with the system, how much time the user is spending with the system, whether the user is engaging with the system as expected, and/or any other suitable passive feedback. The feedback can also include active feedback such as the user's input to interactive content, selections within content, and/or any other suitable active feedback. The feedback can also include device data such as location data, sensor data, and the like.

In this example, the server computer 122 or, in some examples, the computing device 110 uses the feedback data to further personalize the content of program of content 806 by removing the original subset of content sessions 810*b* and replacing them with a dynamically customized subset of content sessions 812. In this example, the number of content sessions in the customized subset of content sessions 812 is greater than the number in the original subset of content sessions 810*b*. In other examples, the customized subset may be smaller, or may be entirely excluded.

Following T=1, the user will begin working through the customized subset of content sessions 812. Between T=1 and T=2, the user has completed three out of the four customized subset of content sessions 812, and is at node 814*a* of content graph 816. But, at T=2, the computing device 110 provides feedback 822*b* to the server computer 122. This feedback can include any of the feedback described with respect to T=1.

In this example, the server computer 122 or, in some examples, the computing device 110 uses the feedback data received at T=2 to further personalize the content of a particular content session by removing a branch of the content graph 816, i.e., node 814*b* and corresponding branch, and replacing it with a new branch including node 814*c*. Thus, following T=2, the user will proceed to the node 814*c*, instead of the node 814*b*. In this manner, the program of content 806 may be customized to a user at a content session level, i.e., by removing, adding, and/or adjusting relationships between nodes 814 of a content session.

Following T=2, the user will proceed to the node 814*c*, at which the computing device 110 will begin to present original content items 818 to the user. Between T=2 and T=3, the user has completed at least some of the original content items 818 within the content node 814*c*. But, at T=3, the computing device 110 provides feedback 822*c* to the server computer 122. This feedback can include any of the feedback described with respect to T=1.

In this example, the server computer 122 or, in some examples, the computing device 110 uses the feedback data received at T=3 to further personalize the content of a particular node, i.e., the node 814*c* in this example, by removing content items 818, adding new content items 820, and/or otherwise dynamically adjusting the original content items 818. In this example, the new content item 820 has been added to the node 814*c* after the user has begun viewing and/or interacting with the other content items 818 of the node 814*c*. In this manner, the program of content 806 may be customized to a user at a node level, i.e., by removing, adding, and/or adjusting content items 818 and 820 of the node 814*c*, even while the user is interacting with the other content items.

FIGS. 9-12 illustrate example flow diagrams showing processes 900, 1000, 1100, and 1200, according to at least a few examples. These processes, and any other processes described herein (e.g., the processes 402 and 502), are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer readable storage medium, for example, in the form of a computer program including a plurality of instructions executable by one or more processors.

Figure 9:
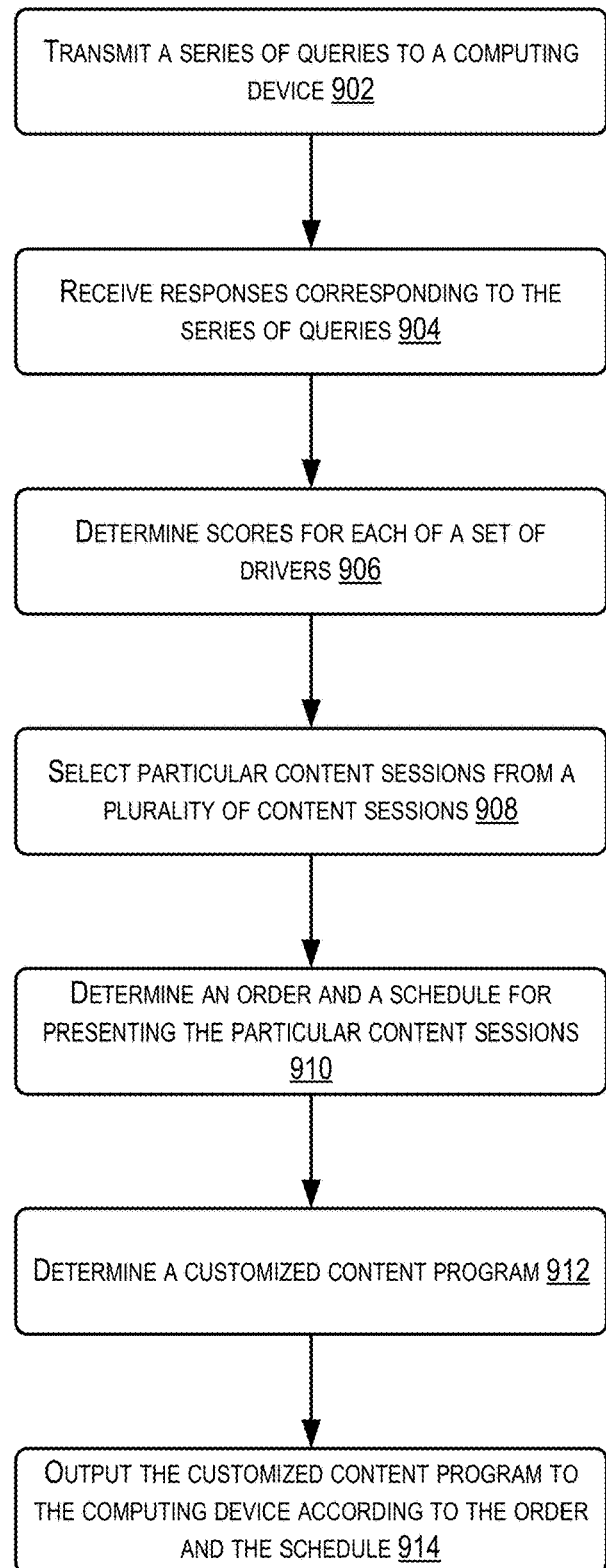
FIG. 9 includes an example flowchart illustrating a process for generating and transmitting customized programs of content to computing devices, according to at least one example.

FIG. 9 includes an example flowchart illustrating a process 900 for generating and transmitting customized programs of content to computing devices, according to at least one example. The process 900 is performed by the customization engine 164 (FIG. 1) of the server computer 122 (FIG. 1) of the content delivery service 120 (FIG. 1). The process 900 in particular corresponds to generating a customized (e.g., user-specific) content program based on a set of scores derived from responses to user queries.

The process 900 begins at block 902 by the server computer 122 transmitting a series of queries to a computing device such as the computing device 110. A first set of queries of the series of queries may be of a first query type (e.g., queries that are derived from researched psychological screening questionnaires.). The computing device 110 may display the series of queries in an application executing on the computing device. For example, the application may include software for interacting with the server computer 122 to request data, receive data, generate an user interface, and receive and output information using the interface. In some examples, a second set of queries from the series of queries may be of a second type for determining a manner in which a user frames the user's particular psychological issues. This set second set of queries may be used to learn appropriate language to include in the content that is identifying for the user. In some examples, a third set of queries from the series of queries may be of a third type for relating to a user.

At block 904, the process 900 includes the server computer 122 receiving responses to the series of queries. The server computer 122 may receive the responses from the computing device 110. In some examples, the server computer 122, at block 904, receives a subset of response or all responses to the series of queries.

At block 906, the process 900 includes the server computer 122 determining scores for each of a set of drivers. Determining the scores may be based on the responses received at block 904. In some examples, each driver may include a factor associated with one or more psychological issues. The set of drivers may be associated with a plurality of content sessions. At least one content session of the plurality of content sessions may include a multimedia presentation relating to CBT. In some examples, one or more of the drivers may be associated with multiple different psychological disorders. In some examples, each driver from the set of drivers may be associated with a plurality of content programs. In some examples, a score for a driver may be determined using a sum of weights assigned to the responses to the series of queries. In some examples, a score for a driver may be determined using a machine learning model that is trained using historical data including responses to the series of queries and finding resulting from the responses.

At block 908, the process 900 includes the server computer 122 selecting particular content sessions from the plurality of content sessions. Selecting the particular content sessions may be based on the scores and any other information relating to the user. Selecting the particular content sessions may include accessing a mapping that associates drivers and/or driver scores with content sessions.

At block 910, the process 900 includes the server computer 122 determining an order and a schedule for presenting the particular content sessions. Determining the order may be based on the scores and drivers associated with the particular content sessions. In some examples, the order may include an order in which to present the particular content sessions. In some examples, the schedule may include dates or times when each content session from the particular content sessions is to be delivered to the computing device and/or presented at the computing device.

At block 912, the process 900 includes the server computer 122 determining a customized content program. Determining the customized content program may be based on the particular content sessions, the order, and the schedule for presenting the particular content sessions. In some examples, the customized content program may be specific to the user that submitted the responses to the series of queries. Thus, the customized content program may be customized.

At block 914, the process 900 includes the server computer 122 outputting the customized content program to the computing device according to the order and the schedule. This may include sending one or more of the particular content sessions along with instructions for when to present the particular content sessions. In some examples, to conserve storage space on the computing device, the server computer 122 may provide the particular content sessions and/or nodes and/or content items in an on-demand arrangement. For example, the content may be requested by the computing device 110 when needed, which may include streaming certain content such as audio and video.

In some examples, the process 900 may further include determining, by the server computer 122, a first driver from the set of drivers that has a highest score, selecting, by server computer 122, a particular content program from a plurality of content programs associated with the first driver, using, by the server computer 122, the particular content program to select the particular content sessions, and using, by server computer 122, the particular content program to determine the order and the schedule.

In some examples, the process 900 may further include determining, by the server computer 122, a first driver from the set of drivers that has a highest score, and determining, by the server computer 122, a second driver from the set of drivers that has a second highest score. The particular content sessions may be selected from a first content program associated with the first driver and a second content program associated with the second driver.

In some examples, the process 900 may further include the server computer 122 receiving, from the computing device 110, data such as feedback data corresponding to user input at a user interface of the application. The data may include at least one of a record of each occurrence of the application being launched, a response to a query presented when the application is launched, or a comparison of when the particular content sessions were output by the application to the schedule of the customized content program. In some examples, the process 900 may further include the server computer 122 modifying, based on the data, the particular content sessions included in the customized content program, or adjusting, based on the data, the order or the schedule of the particular content sessions.

Figure 10:
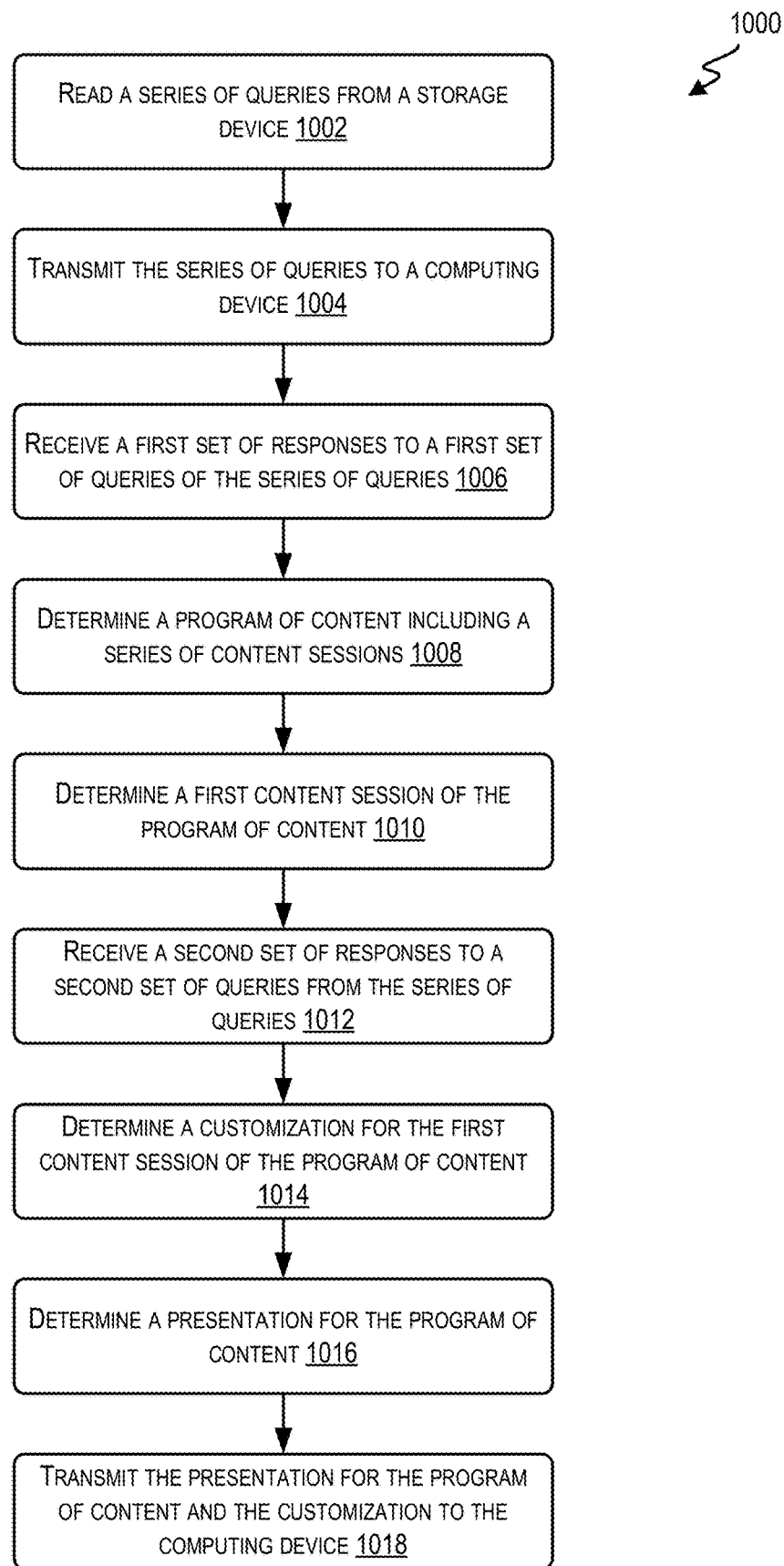
FIG. 10 includes an example flowchart illustrating a process for generating and transmitting customized programs of content to computing devices, according to at least one example.

FIG. 10 includes an example flowchart illustrating a process 1000 for generating and transmitting customized programs of content to computing devices, according to at least one example. The process 1000 is performed by the customization engine 164 (FIG. 1) of the server computer 122 (FIG. 1) of the content delivery service 120 (FIG. 1). The process 1000 in particular corresponds to determining a customization for a program of content based on at least two sets of responses to queries.

The process 1000 begins at block 1002 by the server computer 122 reading a series of queries from a storage device. The storage device may be associated with a content delivery service that includes the server computer 122 such as the query data database 154.

At block 1004, the process 1000 includes the server computer 122 transmitting the series of queries to a computing device such as the computing device 110. This may be performed similar to block 902. Thus, the series of queries may include multiple sets of queries of different query types. In some examples, the computing device 110 may display the series of queries in an application executing on the computing device 110. Each query may be displayed with a prompt for a response. In some examples, one or more queries from the series of queries may use different words to ask for a same information.

At block 1006, the process 1000 includes the server computer 122 receiving a first set of responses to a first set of queries from the series of queries. The first set of queries may be received from the computing device 110. The first set of queries may be of a first type.

At block 1008, the process 1000 includes the server computer 122 determining a program of content including a series of content sessions. Determining the program of content may be based on the first set of responses. In some examples, each content session may be related to CBT and may include at least one of an audio segment, a video segment, an interactive multimedia module, a question, or any other content item.

In some examples, the process 1000 includes determine, by the server computer 122 and using the first set of responses, scores for each of a set of drivers. In this example, each driver may include a factor associated with one or more psychological issues. The set of drivers may be associated with the series of content sessions. In this example, determining the program of content may include determining the program of content based on the set of drivers.

At block 1010, the process 1000 includes the server computer 122 determining a first content session of the program of content. Determining the first content session may be based on the first set of responses. The first content session may be presented at the computing device 110. The first content session may be the first to be presented in an order or may be one of the content sessions of the program of content.

At block 1012, the process 1000 includes the server computer 122 receiving a second set of responses to a second set of queries from the series of queries. Receiving the second set of responses may include receiving the response from the computing device. The second set of queries may be of a second type.

In some examples, determining the program of content may include determining the program of content using the second set of responses. In some examples, determining the program of content may include using a machine learning model.

In some examples, at least one of the audio segment, the video segment, the interactive multimedia module, or the query include words that a user indicated, in the first set of responses or the second set of responses, as describing the user's psychological issues.

At block 1014, the process 1000 includes the server computer 122 determining a customization for the first content session of the program of content. Determining the customization may be based on at least one of the first set of responses or the second set of responses. For example, developing the program of content may be dynamic in the sense that as additional responses are received and/or other feedback information is received, aspects of the program of content may be modified. In some examples, determining the customization for the first content session may include determining a customized combination and order of content items comprising audio segments, video segments, interactive multimedia modules, or questions. In this example, the content items may be associated with the first content session.

At block 1016, the process 1000 includes the server computer 122 determining a presentation for the program of content. The presentation for the program of content may include information relating to the look and feel of the program of content. This may be customized and/or configured based on information known about the user. In some examples, the presentation for the program of content may modify the appearance of the first content session without modifying information included in the first content session. In some examples, determining the presentation may be based on contextual information include user demographic information, location information derived from the computing device, or any other suitable feedback data.

At block 1018, the process 1000 includes the server computer 122 transmitting the presentation for the program of content and the customization for the first content session to the computing device 110. In some examples, the computing device 110 may render the presentation in a context layer of the application. The context layer of the application may be configured to modify an appearance of the first content session using the presentation.

In some examples, queries such as the series of queries may be stored on the storage device in a graph structure. In this example, the process 1000 may further include determining the second set of queries by at least selecting, at a node in the graph structure, a branch associated with a response of the first set of responses. In some examples, the process 1000 may further include determining the second set of queries based on the first set of responses.

In some examples, modifying the appearance of the first content session may include the context layer modifying the appearance of the first content session to include contextual information of a user associated with the computing device 110.

In various examples, to determine modifications or adjustments to the content program, the content delivery service may calculate updated scores for drivers. To determine updated scores, the content delivery service can, for example, prompt the user to response the initial onboarding queries again. Alternatively or additionally, the content delivery service may incorporate the data collected as the user interacts with the users content program.

Figure 11:
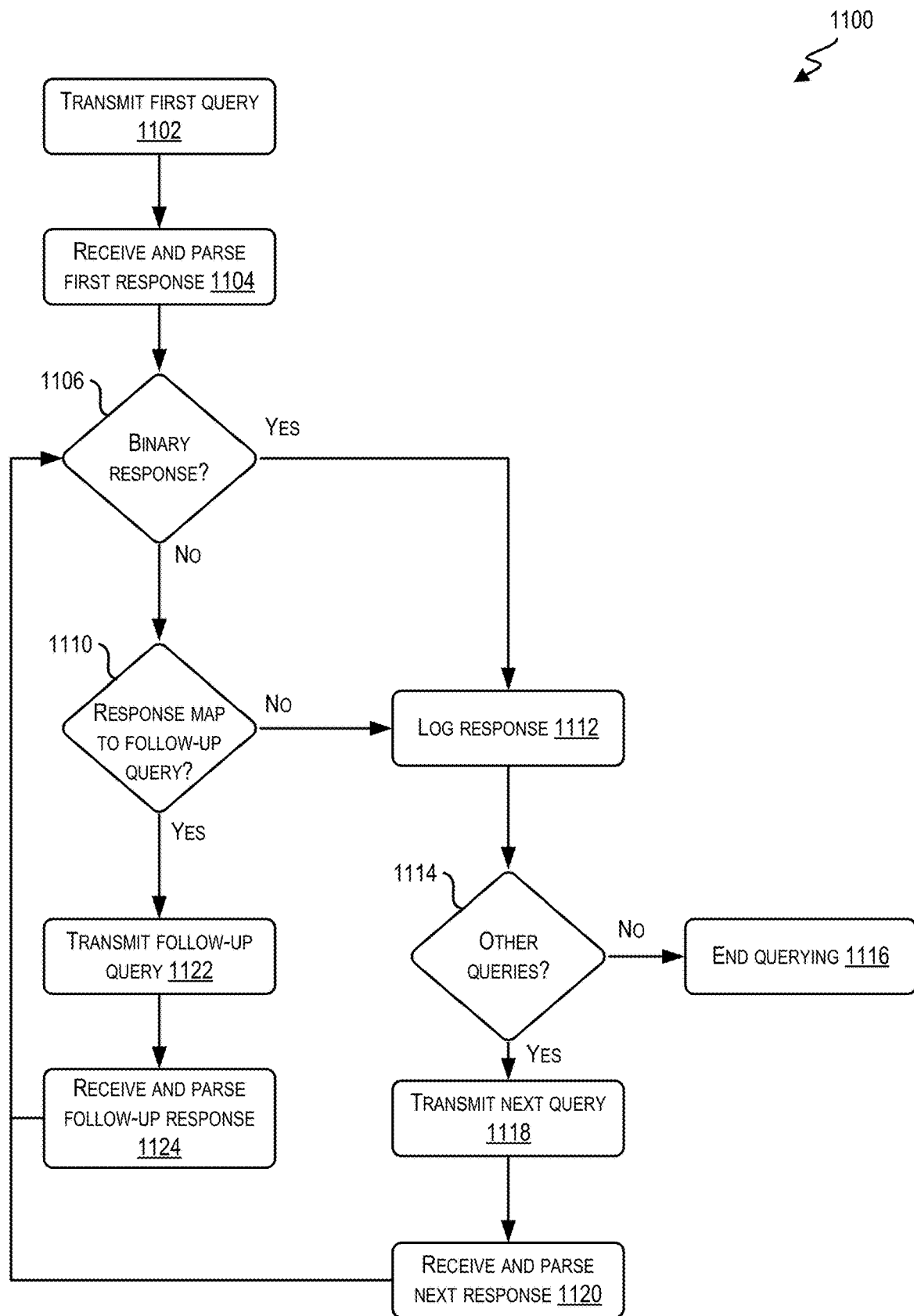
FIG. 11 includes an example flowchart illustrating a process for obtaining context-sensitive information for generating customized programs of content, according to at least one example.

FIG. 11 includes an example flowchart illustrating a process 1100 for obtaining context-sensitive information for generating customized programs of content, according to at least one example. The process 1100 is performed by the customization engine 164 (FIG. 1) of the server computer 122 (FIG. 1) of the content delivery service 120 (FIG. 1). In particular, the process 1100 may implement an adaptive questioning system that seeks a user's particular language for describing her problems, in addition to asking queries that can be used for determining the user's drivers. Different people can describe the same condition in different ways, and may not recognize, or want to acknowledge, that they have a condition. This system poses queries and, based on the responses, will change the queries until the system lands on the user's own way of framing her issues. The system also integrates queries that are needed to formulate a finding for the user, and puts these queries within the context of the overall line of querying, so that the user is more likely to give a truthful response. The result of the queries can be used both to determine the user's drivers, and to develop a contextual framework for the particular user, which can then be used to present content to the user.

The process 1100 begins at block 1102 by the server computer 122 transmitting a first query. The first query may be accessed from a storage device such as the query data database 154. The first query may be transmitted to the computing device 110 and presented by the computing device 110 within an application.

At 1104, the process 1100 includes the server computer 122 receiving and parsing a first response. The first response may be received from the computing device 110, e.g., as an input received via the application. The first response may be responsive to the first query. Parsing the first response may include using a parsing algorithm to review the content of the first response.

At 1106, the process 1100 includes the server computer 122 determining whether the first response is a binary response. This may include determining whether the first query required a binary response (e.g., yes/no, true/false, high/low, good/bad, etc.), and determining whether the parsed first response includes a response that is binary.

If the first response is not binary (e.g., answer at 1106 is "No"), the process 1100 proceeds to 1110, at which, the process 1100 includes the server computer 122 determining whether the first response maps to a follow-up query. This may include traversing a query graph to identify whether a next node in the question graph identifies a follow-up question.

If the first response does not map to a follow-up query (e.g., answer at 1110 is "No"), the process 1100 proceeds to 1112, at which, the process 1100 includes the server computer 122 logging the response. Logging the response may include storing the response (and associated query) in association with the user profile, or at least in manner that the response may be accessed for computing driver scores, determining programs of content, identifying content sessions, and customizing the same, as described herein.

If the first response is binary (e.g., answer at 1106 is "Yes"), the process 1100 also proceeds to 1112, at which, the process 1100 includes the server computer 122 logging the response.

After logging the response at 1112, the process 1100 proceeds to 1114, at which, the process 1100 includes the server computer 122 determining whether there are other queries. This may include accessing the question graph to see if there are other branches and/or nodes to traverse. In some examples, the queries may be stored in an order list, which may be processed using a set of rules.

If there are no more queries (e.g., answer at 1114 is "No"), the process 1100 proceeds to 1116 and ends. If there are more queries (e.g., answer at 1114 is "Yes"), the process 1100 proceeds to 1118, at which, the process 1100 includes the server computer transmitting a next query. This may be performed similar as block 1102. The process 1100 also includes the server computer 122 receiving and parsing the next response at 1120, similarly as block 1104. The process 1100 then returns to the binary response check at 1106.

Returning to block 1110, if the first response maps to a follow-up query (e.g., the answer at 1110 is "Yes"), the process 1100 proceeds to 1122, at which, the process 1100 includes the server computer 122 transmitting a follow-up query. The follow-up query may be indicated by the question graph and/or may be otherwise derived from the first response.

At block 1124, the process 1100 includes the server computer 122 receiving and parsing the follow-up response, similarly as block 1104. The process 1100 then returns to the binary response check at 1106.

Figure 12:
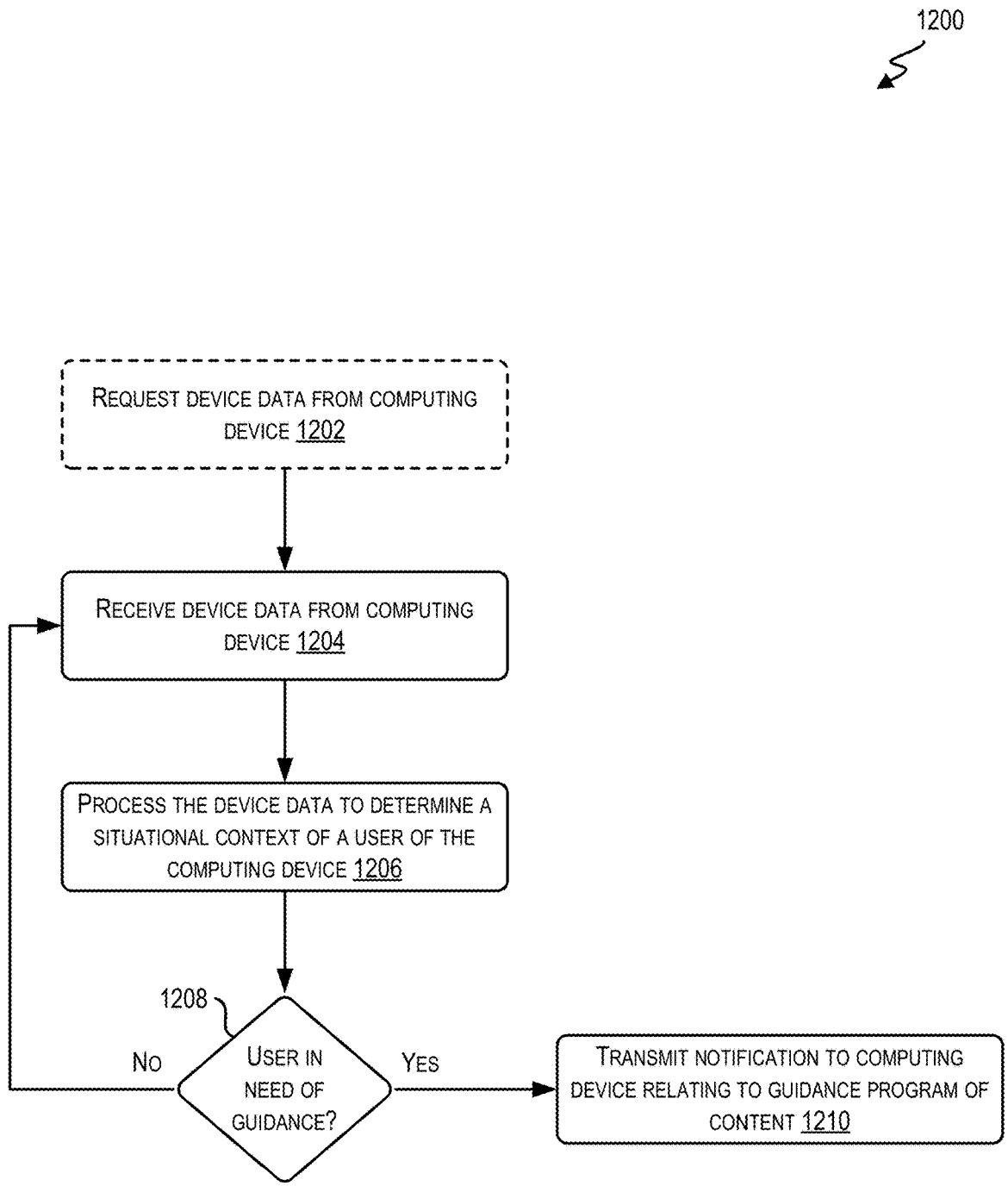
FIG. 12 includes an example flowchart illustrating a process for transmitting customized programs of content depending on situational context, according to at least one example.

FIG. 12 includes an example flowchart illustrating a process 1200 for transmitting customized programs of content depending on situational context, according to at least one example. The process 1200 is performed by the customization engine 164 (FIG. 1) of the server computer 122 (FIG. 1) of the content delivery service 120 (FIG. 1). In particular, the process 1200 may implement an aspect of computer application that keeps track of a user's situation at all times, and determines whether the user needs or would benefit from CBT at any given moment. The application can use information from a smartphone, such as data derived from geolocation devices, accelerometers, gyroscopes, heart rate monitors, smart watches, etc. to determine the user's current situational context (e.g., what she's doing, where she's going, what's nearby, how is she reacting to what's going on around her, etc.). From the situational context, the system can determine whether the user is currently in, or is entering into a situation for which she needs cognitive guidance. Alternatively, the system can determine that the user is in good situation for practicing a CBT technique, and can prompt the user to take steps to practice the technique. The system can thus be proactive in the user's treatment.

The process 1200 begins at block 1202 by the server computer 122 requesting device data from a computing device such as the computing device 110. In some examples, block 1202 may be optionally included in the process 1200. For example, the computing device 110 may provide the device data without the server computer 122 requesting the data. In some examples, the computing device 110 provides the data according to some fixed interval such as every few minutes, every few hours, once a day, every few days, etc. In some examples, the computing device 110 provides the data in accordance with one or more triggers, etc. when the user's heartrate exceeds some threshold, when the computing device 110 is plugged in and connected to WiFi, when the user's calendar is open, etc.

At 1204, the process 1200 includes the server computer 122 receiving device data from the computing device 110. The device data may include any suitable feedback data and/or other such data including health data, sensor data, location data, etc.

At 1206, the process 1200 includes the server computer 122 processing the device data to determine a situational context of a user of the computing device 110. This may include the server computer 122 inputting at least some of the data received at 1204 into a predictive model and determining, based on output from the model, the situational context. The situational context may indicate contextual information about the user and her situation such as, for example, where she is located, whether she is moving (e.g., has been moving, is likely to not move for some period of time), whether she is likely free (e.g., calendar is open, not talking on the phone, etc.), who she is with, what she might be doing (e.g., location data of the computing device 110 may be correlated with map data of surrounding area to determine draw conclusions about what the user may be doing, heart rate data or other health-related data may be accessed to determine whether the user is physical active or has an elevated heartrate), and any other contextual information about the user.

At 1208, the process 1200 includes the server computer 122 determining whether the user is in need of guidance. This may include comparing the user's progress in a program of content with the situational context. For example, the server computer 122 may publish or otherwise make available a set of situational guidance tasks. Each situational guidance task may include a corresponding set of conditions which, when true, identify an opportunity to perform the task. The process 1200 may check the published tasks, evaluate the set of conditions, and based on the evaluating proceed to either 1210 or 1212.

If the user is in need of guidance (e.g., the answer at 1208 is "Yes"), the process 1200 proceeds to 1210, at which, the process 1200 transmits notification to the computing device 110 relating to a guidance program of content. For example, one aspect of the user's program of content is to visit a crowded location, the process 1200 may send a push notification to the user's mobile device when she is walking past a location with many people (e.g., an outdoor market or park). The notification may inform the user that performing some objective at the location may fulfill the corresponding requirement in the program of content.

If the user is not in need of guidance (e.g., the answer at 1208 is "No"), the process 1200 returns to 1204, at which, the process 1200 receives device data from the computing device 110.

Specific details were given in the preceding description to provide a thorough understanding of various implementations of systems and components for a transdiagnostic digital medicine system. It will be understood by one of ordinary skill in the art, however, that the implementations described above may be practiced without these specific details. For example, circuits, systems, networks, processes, and other components may be shown as components in block diagram form in order not to obscure the examples in unnecessary detail. In other instances, well-known circuits, processes, algorithms, structures, and techniques may be shown without unnecessary detail in order to avoid obscuring the examples.

It is also noted that individual implementations may be described as a process which is depicted as a flowchart, a flow diagram, a data flow diagram, a structure diagram, or a block diagram. Although a flowchart may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

The various examples discussed above may further be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a computer-readable or machine-readable storage medium (e.g., a medium for storing program code or code segments). A processor(s), implemented in an integrated circuit, may perform the necessary tasks.

Where components are described as being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

The various illustrative logical blocks, modules, circuits, and algorithm steps described in connection with the implementations disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The techniques described herein may also be implemented in electronic hardware, computer software, firmware, or any combination thereof. Such techniques may be implemented in any of a variety of devices such as general purposes computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for a content delivery system.

What is claimed is:

1. A computer-implemented method for content delivery, comprising:

generating, by a content delivery service executing on a computing system, a first query based at least in part on contextual information of a user, wherein the first query is configured to screen for one or more psychological disorders;

transmitting, by the content delivery service, the first query for presentation in an application executing on a computing device associated with the user, wherein the first query is of a first query type and comprises a first prompt requesting a first user response;

receiving, by the content delivery service and from the computing device, the first user response to the first query;

generating, by the content delivery service, a second query based at least in part on first content of the first user response, wherein the second query is of a second query type and is configured to screen for the one or more psychological disorders of the user;

transmitting, by the content delivery service, the first second query for presentation in the application executing on the computing device associated with the user, wherein the second query comprises a second prompt requesting a second user response;

receiving, by the content delivery service and from the computing device, the second user response to the second query;

generating, by the content delivery service, a customized content program based at least in part on the second user response to the second query, the customized content program configured to direct the user through exercises to address the one or more psychological disorders; and outputting, by the content delivery service, the customized content program to the computing device.

2. The computer-implemented method of claim 1, further comprising parsing, by the content delivery service, first content of the first user response to identify one or more terms included in the first content of the first user response and used by the user to respond to the first prompt, and wherein generating the second query based at least in part on the first content of the first user response comprises generating the second query based at least in part on the one or more terms such that at least one term of the one or more terms is included in the second query.

3. The computer-implemented method of claim 2, wherein the at least one term represents terminology the user has used to refer to the one or more psychological orders.

4. The computer-implemented method of claim 1, wherein generating the first query comprises selecting the first query from a set of queries based at least in part on the contextual information.

5. The computer-implemented method of claim 4, wherein generating the second query comprises changing one query of the set of queries to define the second query based at least in part on first content of the first user response.

6. The computer-implemented method of claim 1, wherein generating the first query and generating the second query are based at least in part on a question graph comprising a plurality of branches and a plurality of nodes.

7. One or more non-transitory computer-readable media comprising computer-executable instructions that, when executed by one or more processors, cause the one or more processors to perform operations comprising:

generating, by a content delivery service executing on a computing system, a first query based at least in part on contextual information of a user, wherein the first query is configured to screen for one or more psychological disorders;

transmitting, by the content delivery service, the first query for presentation in an application executing on a computing device associated with the user, wherein the first query is of a first query type and comprises a first prompt requesting a first user response;

receiving, by the content delivery service and from the computing device, the first user response to the first query;

generating, by the content delivery service, a second query based at least in part on first content of the first user response, wherein the second query is of a second query type and is configured to screen for the one or more psychological disorders;

transmitting, by the content delivery service, the second query for presentation in the application executing on the computing device associated with the user, wherein the second query comprises a second prompt requesting a second user response;

receiving, by the content delivery service and from the computing device, the second user response to the second query;

generating, by the content delivery service, a customized content program based at least in part on the second user response to the second query, the customized content program configured to direct the user through exercises to address the one or more psychological disorders; and outputting, by the content delivery service, the customized content program to the computing device.

8. The one or more non-transitory computer-readable media of claim 7, wherein the computer-readable media comprise further computer-executable instructions that, when executed by the one or more processors, cause the one or more processors to perform additional operations comprising determining, by a machine learning model of the content delivery service and using the first user response and the second user response, scores for each of a set of drivers, wherein each driver of the set of drivers comprises a factor associated with the one or more psychological disorders.

9. The one or more non-transitory computer-readable media of claim 8, wherein the customized content program comprises one or more content sessions, and wherein each content session of the one or more content sessions is associated with at least one driver of the set of drivers.

10. The one or more non-transitory computer-readable media of claim 9, wherein generating the customized content program comprises generating the customized content program based at least in part on respective drivers associated with content sessions of the one or more content sessions.

11. The one or more non-transitory computer-readable media of claim 8, wherein the machine learning model is trained using historical data including other responses to different sets of queries and findings resulting from the other responses.

12. The one or more non-transitory computer-readable media of claim 7, wherein the computer-readable media comprise further computer-executable instructions that, when executed by the one or more processors, cause the one or more processors to perform additional operations comprising parsing, by the content delivery service, first content of the first user response to identify one or more terms included in the first content of the first user response and used by the user to respond to the first prompt, and wherein generating the second query based at least in part on the first content of the first user response comprises generating the second query based at least in part on the one or more terms such that at least one term of the one or more terms is included in the second query.

13. The one or more non-transitory computer-readable media of claim 12, wherein the at least one term represents terminology the user has used to refer to the one or more psychological orders.

14. The one or more non-transitory computer-readable media of claim 7, wherein generating the first query comprises selecting the first query from a set of queries based at least in part on the contextual information.

15. A computing system of a content delivery service, comprising:

one or more processors; and one or more non-transitory computer-readable media comprising computer-executable instructions that, when executed by the one or more processors, cause the one or more processors to at least:

generate a first query based at least in part on contextual information of a user, wherein the first query is of a first query type and is configured to screen for one or more psychological disorders of the user;

transmit the first query for presentation in an application executing on a computing device associated with the user, wherein the first query comprises a first prompt requesting a first user response;
receive, from the computing device, the first user response to the first query;
generate a second query based at least in part on first content of the first user response, wherein the second query is of a second query type and is configured to screen for the one or more psychological disorders of the user;
transmit the second query for presentation in the application executing on the computing device associated with the user, wherein the second query comprises a second prompt requesting a second user response;
receive, from the computing device, the second user response to the second query;
generate a customized content program based at least in part on the second user response to the second query, the customized content program configured to direct the user through exercises to address the one or more psychological disorders; and
output the customized content program to the computing device.

16. The computing system of claim 15, wherein the computer-executable instructions, when executed by the one or more processors, further cause the one or more processors to parse first content of the first user response to identify one or more terms included in the first content of the first user response and used by the user to respond to the first prompt, and wherein generating the second query based at least in part on the first content of the first user response comprises generating the second query based at least in part on the one or more terms such that at least one term of the one or more terms is included in the second query.

17. The computing system of claim 16, wherein the at least one term represents terminology the user has used to refer to the one or more psychological orders.

18. The computing system of claim 15, wherein generating the first query comprises selecting the first query from a set of queries based at least in part on the contextual information.

19. The computing system of claim 18, wherein generating the second query comprises changing one query of the set of queries to define the second query based at least in part on first content of the first user response.

20. The computing system of claim 15, wherein generating the first query and generating the second query are based at least in part on a question graph comprising a plurality of branches and a plurality of nodes.

* * * * *